US009305762B2

(12) United States Patent
Covey et al.

(10) Patent No.: US 9,305,762 B2
(45) Date of Patent: Apr. 5, 2016

(54) MASS ANALYSIS SYSTEM WITH LOW PRESSURE DIFFERENTIAL MOBILITY SPECTROMETER

(71) Applicant: DH Technologies Development Pte. Ltd., Singapore (SG)

(72) Inventors: Thomas R. Covey, Richmond Hill (CA); Bradley B. Schneider, Bradford (CA)

(73) Assignee: DH Technologies Development Pte. Ltd., Singapore (SG)

( * ) Notice: Subject to any disclaimer, the term of this patent is extended or adjusted under 35 U.S.C. 154(b) by 351 days.

(21) Appl. No.: 13/693,837

(22) Filed: Dec. 4, 2012

(65) Prior Publication Data

US 2013/0092834 A1 Apr. 18, 2013

Related U.S. Application Data

(62) Division of application No. 13/016,257, filed on Jan. 28, 2011, now abandoned.

(60) Provisional application No. 61/299,086, filed on Jan. 28, 2010.

(51) Int. Cl.
*G01N 24/00* (2006.01)
*H01J 49/26* (2006.01)
*G01N 27/62* (2006.01)
*H01J 49/00* (2006.01)

(52) U.S. Cl.
CPC .............. *H01J 49/26* (2013.01); *G01N 27/624* (2013.01); *H01J 49/004* (2013.01); *Y10T 436/24* (2015.01)

(58) Field of Classification Search
None
See application file for complete search history.

(56) References Cited

U.S. PATENT DOCUMENTS

| 5,432,343 | A | 7/1995 | Gulcicek et al. |
| 7,164,122 | B2 | 1/2007 | Fuhrer et al. |
| 2003/0020012 | A1* | 1/2003 | Guevremont ................ 250/287 |
| 2008/0067367 | A1 | 3/2008 | Park |
| 2008/0315087 | A1 | 12/2008 | Wollnik et al. |
| 2009/0294650 | A1 | 12/2009 | Schneider et al. |

FOREIGN PATENT DOCUMENTS

| WO | 2006/085110 | | 8/2006 | |
| WO | WO 2008/005283 | * | 1/2008 | ............. G01N 27/64 |

\* cited by examiner

*Primary Examiner* — Robert Xu

(57) ABSTRACT

A mass analysis system including a low pressure dissociation region and a differential mobility spectrometer. The differential mobility spectrometer including at least one pair of filter electrodes defining an ion flow path where the filter electrodes generate an electric field for passing through a selected portion of the sample ions based on the mobility characteristics of the sample ions. The differential mobility spectrometer also includes a voltage source that provides DC and RF voltages to at least one of the filter electrodes to generate the electric field, an ion inlet that receives sample ions that have passed through the low pressure dissociation region, and an ion outlet that outputs the selected portion of the sample ions. A mass spectrometer receives some or all of the selected portion of the sample ions.

8 Claims, 22 Drawing Sheets

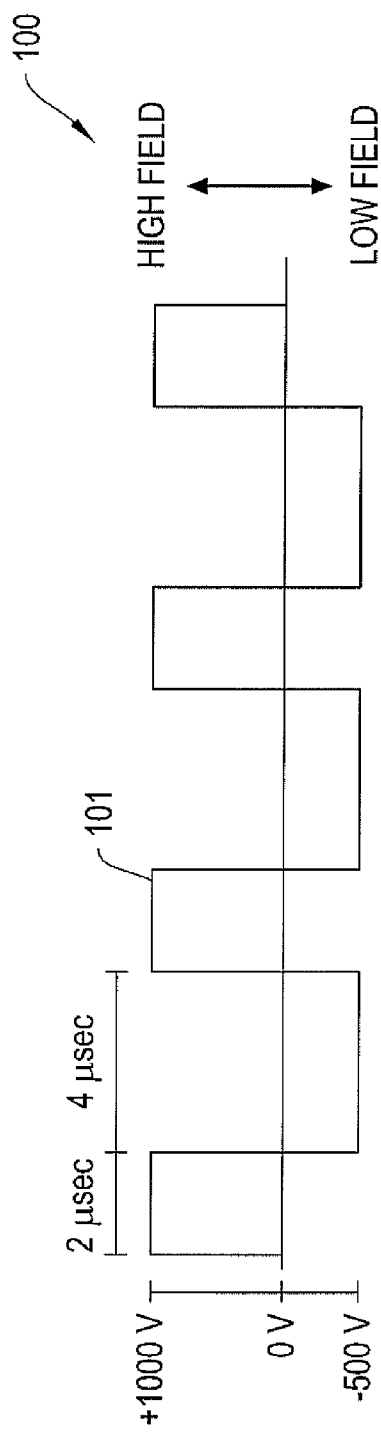
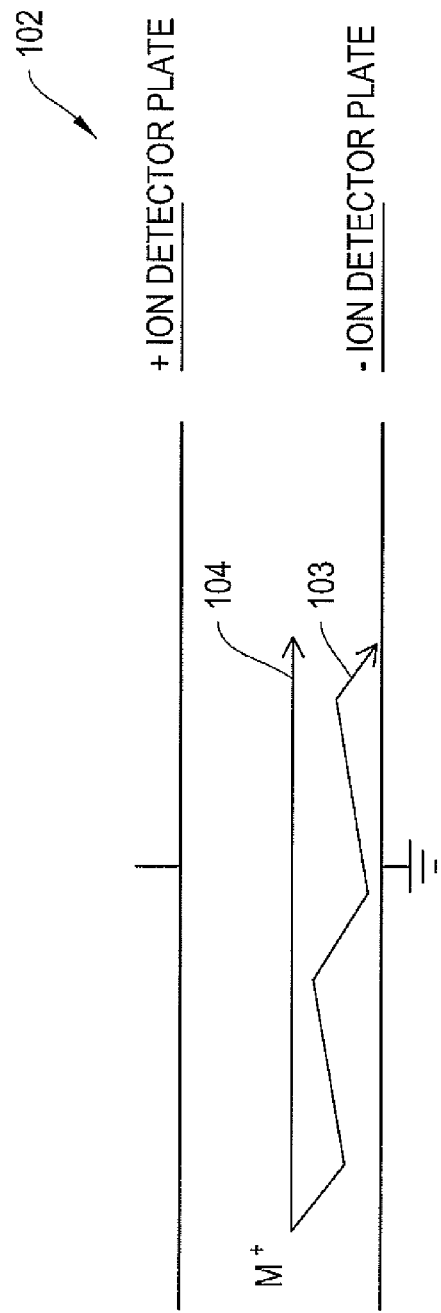
Figure 1A (Prior Art)
Figure 1B (Prior Art)

MASS ANALYSIS SYSTEM WITH LOW PRESSURE DIFFERENTIAL MOBILITY SPECTROMETER

REFERENCE TO RELATED APPLICATIONS

This application is a divisional of U.S. application Ser. No. 13/016,257 filed Jan. 28, 2011 which claims benefit of U.S. Provisional Application No. 61/299,086 filed Jan. 28, 2010 and entitled "Mass Analysis System With Low Pressure Differential Mobility Spectrometer" the entirety of all of which are incorporated herein by reference.

INTRODUCTION

A Differential Mobility Spectrometer (DMS), also referred to as a Field Asymmetric Waveform Ion Mobility Spectrometer (FAIMS) or Field Ion Spectrometer (FIS), typically performs gas phase ion sample separation and analysis. In some circumstances, a DMS has been interfaced with a mass spectrometer (MS) to take advantage of the atmospheric pressure, gas phase, and continuous ion separation capabilities of the DMS and the detection accuracy of the MS.

By interfacing a DMS with an MS, numerous areas of sample analysis, including proteomics, peptide/protein conformation, pharmacokinetic, and metabolism analysis have been enhanced. In addition to pharmaceutical and biotech applications, DMS-based analyzers have been used for trace level explosives detection and petroleum monitoring.

A DMS, like an ion mobility spectrometer (IMS), is considered an ion mobility based analyzer because the DMS separates and analyzes ions based on the mobility characteristics of the ions. In an IMS, ions are pulsed into and pass through a drift tube while being subjected to a constant electric field. The ions interact with a drift gas in the drift tube and the interactions affect the time it takes for the sample ions to pass through the drift tube, e.g., the time-of-flight (TOF). These interactions are specific for each analyte ion of a sample, leading to an ion separation based on more than just mass/charge ratio. In contrast, in a TOF MS, there is a vacuum in the drift region of the MS and, therefore, an ion's time through the MS drift region is based on the ion's mass-to-charge ratio (m/z) in the collision-free environment of the vacuum.

A DMS is similar to an IMS in that the ions are separated in a drift gas. However, unlike an IMS, the DMS uses an asymmetric electric field waveform that is applied between at least two parallel electrodes through which the ions pass, typically, in a continuous manner. The electric field waveform typically has a high field duration at one polarity and then a low field duration at an opposite polarity. The duration of the high field and low field portions are applied such that the net voltage being applied to the DMS filter electrodes is zero.

FIG. 1A shows a plot 100 of the time-varying, RF, and/or asymmetric high and low voltage waveform 101 (e.g., Vrf) that can be applied to generate an asymmetric electric field. FIG. 1B shows a diagram of a DMS filter 102 where the path of an ion $M^+$ is subjected to an asymmetric electric field resulting from the asymmetric voltage waveform 101. The ion's mobility in the asymmetric electric field indicates a net movement 103 towards the bottom electrode plate of the DMS filter 102. This example shows that, in a DMS, an ion's mobility is not constant under the influence of the low electric field compared to the high electric field. Since an ion may experience a net mobility towards one of the filter electrode plates during its travel between the plates, a compensation voltage (Vc) is applied to the filter electrodes to maintain a safe trajectory 104 for the ion through the DMS filter 102 without striking one of the filter electrodes. The ions are passed between the two filter electrodes by either being pushed through with a pressurized gas flow upstream of the filter electrodes or pulled through by a pump downstream from the filter electrodes.

In a DMS or IMS, ions are typically separated in a gas at pressures sufficient to enable collisions between sample ions and neutral drift gas molecules. The smaller the ion, the fewer collisions it will experience as it is pulled through the drift gas. Because of this, an ion's cross sectional area can effect the ion's mobility through the drift gas. As shown in FIG. 1B, an ion's mobility is not constant under the influence of a low electric field compared to a high electric field. This difference in mobility may be related to clustering/de-clustering reactions taking place as an ion experiences the weak and strong electric fields. An ion typically experiences clustering with neutral molecules in the drift gas during the weak field portion of the waveform, resulting in an increased cross sectional area. During the strong field portion of the waveform, the cluster may be dissociated, reducing the ion's cross sectional area. Alternatively, differences between high and low field mobility behavior may be due to different collision dynamics due to changes that occur in ion translational energy.

The integration of a DMS with a MS can provide added selectivity that can be used for purposes such as chemical noise reduction and elimination of isobaric interferences. This general reduction of the chemical background can provide improvements in the detection limit (defined for example as $3\sigma$/slope of the calibration curve) for various assays. One of the key factors limiting general applicability of DMS technology with MS analysis is the reduction in instrument sensitivity that is observed upon installation of the DMS. Experiments have demonstrated that the observed sensitivity reduction due to the DMS has a flow rate dependence, with typical values being 3× down at low solvent flows (10 µL/min) and 10× down at high flows (500 µL/min). These sensitivity reductions may occur as a result of three different phenomena: 1) diffusion losses in the DMS itself, 2) inefficiencies in ion transport into and out of the DMS, and 3) ion clustering. Our experiments provide strong evidence that the bulk of losses currently being observed with the DMS at high solvent flows are a result of sampling a "wet spray" into the DMS and subsequently filtering clusters that do not transmit at the same Vc as the unclustered parent ion. This hypothesis is supported by modeling of diffusion behavior, as well as experimental data showing improvements in the coefficient of transmission with additional heaters located in front of the DMS.

In existing DMS-MS systems, there are several approaches where desolvation or declustering are utilized including: 1) the source region where turbo heaters can be operated up to 750° C., 2) a counter-current gas flow region established by the heated curtain gas, and 3) a declustering region within the first vacuum stage where the potential difference between the inlet orifice and first vacuum lens element provides some declustering. Existing DMS-MS systems typically locate the DMS before the orifice of the MS, which results in a limitation in that ions and clusters are filtered prior to the orifice, eliminating the ability to decluster within the first vacuum stage. Elimination of this stage of declustering results in sensitivity reduction with the DMS, with higher solvent flows being most problematic. Efforts to add additional heating and provide additional desolvation prior to the DMS have shown some improvement in sensitivity, however, have imparted very significant challenges with respect to commercialization due to the critical importance of maintaining a constant temperature and the difficulty of monitoring temperature in close proximity to very high AC potentials. The range of assays that can exhibit detection limit improvements with the DMS is limited by the magnitude of the sensitivity reduction that is observed with the DMS device. For instance with a 10× sensitivity reduction, this number may be as low as 5-10%. Mobility based separations have also been known to be of low resolution and limited in peak capacity.

Accordingly, there is a need to improve mobility based resolution and specificity, and to increase the applicability of DMS-MS analyses by providing improved sensitivity and selectivity, including for high flow analyses.

SUMMARY

The application, in various embodiments, addresses the deficiencies of current DMS-MS systems by providing systems and methods including a mass analysis system that combines a MS with a low pressure DMS to enable enhanced sample analysis sensitivity and/or selectivity. In certain aspects, a tandem DMS device advantageously includes first and second DMS filters that utilize separation mechanisms based on two different separation models.

With the tandem device, a cell, including the first DMS, operates at about atmosphere where clustering is done efficiently and a second cell, including the second DMS, operates in a vacuum where declustering to the bare ion is done efficiently. Separation at about atmosphere is done according to a "clusterization model" which derives it's specificity from the differences in the chemical interactions of an ion and its immediate surroundings. For instance, Hydrogen bonding, Vanderwaals forces, steric hindrance, where all of these actions come into play in the clusterization model. The addition of modifiers (e.g., dopants) to the transport gas can assure that separations occur according to this mechanism.

In a vacuum, the tandem device creates dry ions with energetic collisions in, for example, a free jet expansion by accelerating the clusters into a background gas. Because there is a substantially greater mean free path under the vacuum, as compared to atmosphere to accelerate and collide ions, declustering can be done most efficiently in or near the free jet gas expansion. The declustered ions are then separated in the second vacuum DMS according to a "hard sphere collision model". This mechanism is based upon a more "physical" process where the ion mobility is related to the interaction and scattering of ions during collisions with the inert background gas molecules. Ion mobility based separation using the combination of both models advantageously provides orthogonal separation mechanisms that substantially enhance ion analysis with respect to conventional techniques. These and other features of the applicant's teachings are set forth herein.

In one aspect, a mass analysis system includes a low pressure dissociation region, a low pressure DMS that filters sample ions, and a mass spectrometer that receives some or all of the selected portion of the sample ions. The dissociation region may include, without limitation, a collision region, a fragmentation region, an expansion region, a desolvation region, radiation region, high temperature region, and/or the like. The dissociation region may utilize a laser, radiation source, collision gas source, thermal source, gas expansion mechanism, and the like to effect the dissociation process. In one configuration, the DMS includes at least a pair of filter electrodes defining an ion flow path where the filter electrodes generate an electric field for passing through a selected portion of the sample ions based on their ion mobility characteristics. In certain embodiments, the DMS can include a plurality of filter electrode pairs. The DMS also includes a voltage source that provides RF and DC voltages to at least one of the filter electrodes to generate the electric field. The DMS further includes an ion inlet that receives sample ions that have passed through the low pressure collision region and an ion outlet that outputs the selected portion of the sample ions.

In one feature, the low pressure dissociation region is configured to accelerate the sample ions and collide the sample ions with a collision gas. The low pressure dissociation region may be configured to perform at least one of declustering and fragmenting the sample ions. The pressure of the DMS and/or a portion of the low pressure dissociation region may be set at less than about atmospheric pressure. The pressure of the DMS and/or portion of the low pressure dissociation region may be set at about 50 to about 760 Torr. The pressure of the DMS and/or a portion of the low pressure dissociation region may be set at less than about 100 Torr. In certain configurations, the DMS operates from about 200 to about 500 Torr. In certain configurations, the DMS operates at about 200 Torr. In certain configurations, the DMS can operate at less than about 50 Torr, less than about 25 Torr, less than about 15 Torr, less than about 5 Torr, less than about 3 Torr, and less than about 1 Torr. The DMS may be operated at about 2-4 Torr. In one configuration, the pressure of the ion flow path in the DMS is substantially the same as the pressure of a portion of the low pressure dissociation region.

In another feature, the mass analysis system includes at least one ion guide located in at least the low pressure dissociation region or an intermediate region between the low pressure DMS and the low pressure dissociation region. The ion guide may include at least one ion focusing element. The ion focusing element may include an RF rod, RF ring, RF lens, DC lens, DC ring, deflector plate, and/or grid.

The low pressure dissociation region may be configured to receive a flow of the sample ions from an ion source. The ion source may include a second DMS that operates at substantially atmospheric pressure or above. The low pressure dissociation region may be configured to accelerate ions within a free jet expansion. In one configuration, a housing substantially encloses the low pressure DMS and the low pressure dissociation region. The housing may include a housing or vacuum inlet for receiving sample ions. The housing may also include a housing outlet, in communication with an outlet of the low pressure DMS, for outputting a portion of selected sample ions into the mass spectrometer. In various aspects, the ion guide located in the low pressure dissociation region can be removed, and the low pressure DMS can comprise four electrodes.

In another configuration, the mass spectrometer includes at least one ion optics element that receives the selected portion of the sample ions via the housing outlet. The mass spectrometer may include a mass analyzer in communication with at least one ion optics element. In certain features, an insulating material is in communication with and/or supports at least one of the DMS filter electrodes. In certain configurations, the mass analysis system includes one or more heated regions that are configured to perform i) declustering ions, ii) desolvating ions, iii) accelerating the reclustering of ions with reagents, and/or iv) shifting the clustering equilibrium for ions with dopant or reagents.

In another aspect, a sample analysis system includes a first pressure region that operates at a pressure of about atmospheric pressure or greater. The first pressure region includes a first DMS filter that receives sample ions from an ion source and passes through a first set of selected sample ions. The system also includes a second pressure region, in communication with the first pressure region, that operates at less than about atmospheric pressure. The second pressure region includes a dissociation and/or collision region where the first set of selected sample ions are accelerated and collided with a collision gas to desolvate and/or fragment the sample ions. The second pressure region also includes a second DMS filter that passes through a second set of selected sample ions based on their ion mobility characteristics.

In one configuration, the system includes a third pressure region, in communication with the second pressure region, that operates at less than about 1 Torr. The third pressure region may include an ion optics element that receives the second set of selected sample ions. In another configuration, the system includes a fourth pressure region, in communication with the third pressure region, that operates at less than about $10^{-4}$ torr and includes a mass analyzer. In certain embodiments, a vacuum drag is established from a lower pressure region to a higher pressure region to facilitate the transport of ions. For instance, a vacuum drag may be utilized to pull ions into and/or through the first and/or second DMS, or through other components of the ion analyzer.

In another aspect, an ion analysis system comprises an ion inlet and a first low pressure region maintained at a pressure in the range of about 50 to about 760 Torr including a first dissociation region and a differential mobility spectrometer. Second and third low pressure regions maintained at less than about 50 Torr and less than about 1 Torr, respectively, with RF ion guides for directing ions to a fourth low pressure region comprising a mass analyzer.

In a further aspect, an ion analyzer includes an ion source, a flow of ions from the ion source, a reaction region that introduces at least one chemical modifier to the flow of ions, and a first DMS, operating substantially at atmospheric pressure, that receives the flow of ions from the reaction region and performs a first mobility based filter operation on the flow of ions. The analyzer also includes a declustering region, operating at less than atmospheric pressure, that receives the flow of ions from the first DMS. The analyzer further includes a second DMS, operating at less than atmospheric pressure, that receives the flow of ions from the declustering region and performs a second mobility based filter operation on the flow of ions. As discussed above, the ion analyzer may advantageously employ an orthogonal separation approach where the first DMS, operating at about atmospheric pressure, performs ion mobility based separations based on the clusterization model, while the second DMS, operating at less than atmospheric pressure, performs ion mobility based separations based on the hard or rigid sphere collision model. Further details regarding these separation models are provided later herein.

In one configuration, the ion analyzer includes a mass spectrometer that receives the flow of ions from the second DMS. In another configuration, the mass spectrometer includes a mass analyzer. The ion analyzer may include at least one heated region configured to perform at least one of i) declustering ions, ii) desolvating ions, iii) accelerating the reclustering of ions with reagents, and iv) shifting the clustering equilibrium for ions with dopant or reagents.

In yet another aspect, an ion analysis system includes an ion source, a flow of ions from the ion source, a first means for modifying a first portion of ions from the flow of ions to provide a specific $\alpha$-function for each of the ion species associated with the first portion of ions, a first DMS configured to receive the first portion of ions, conduct a differential mobility separation, and output a second portion of ions, a second means for modifying the second portion of ions to alter the $\alpha$ function associated with the second portion of ions, and a second DMS configured to receive the second portion of ions, conduct a differential mobility separation, and output a third portion of ions. The means for modifying may include a reaction region, clustering region, dissociation region, and/or declustering region.

DRAWINGS

The foregoing and other objects and advantages of the invention will be appreciated more fully from the following further description thereof, with reference to the accompanying drawings. The skilled person in the art will understand that the drawings, described below, are for illustration purposes only. The drawings are not intended to limit the scope of the applicant's teachings in any way.

FIG. 1A shows a plot of a time-varying and/or asymmetric high and low voltage waveform that may be applied to generate an asymmetric electric field in a differential mobility spectrometer (DMS);

FIG. 1B shows a diagram of a DMS filter where the path of an ion $M^+$ is subjected to an asymmetric electric field resulting from the asymmetric voltage waveform of FIG. 1A;

Figure 6:
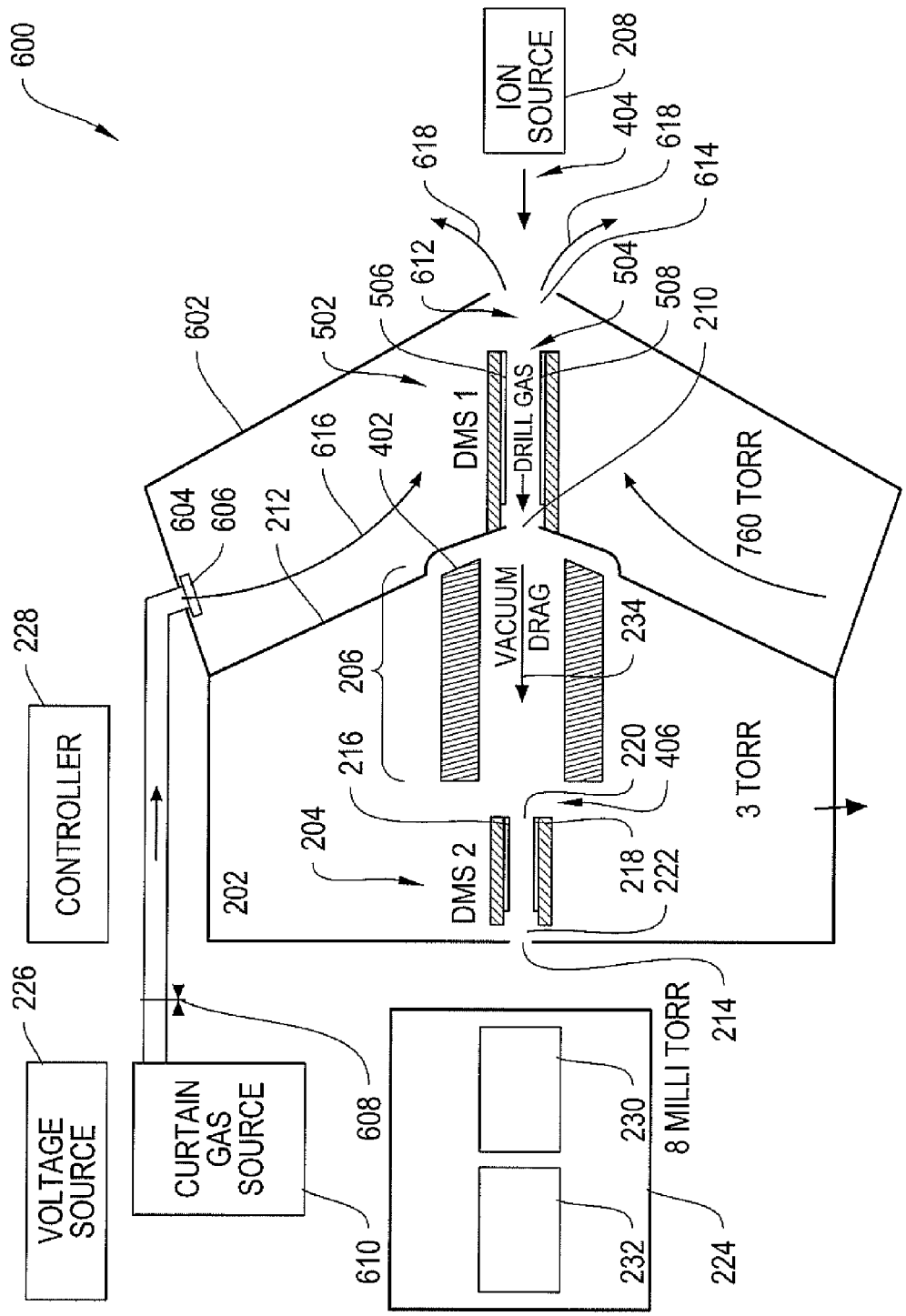
FIG. 6 shows a diagram of a mass analysis system as in FIG. 5A with a clustering and/or reaction region prior to the atmospheric pressure DMS according to an illustrative embodiment of the invention.
Figure 7A:
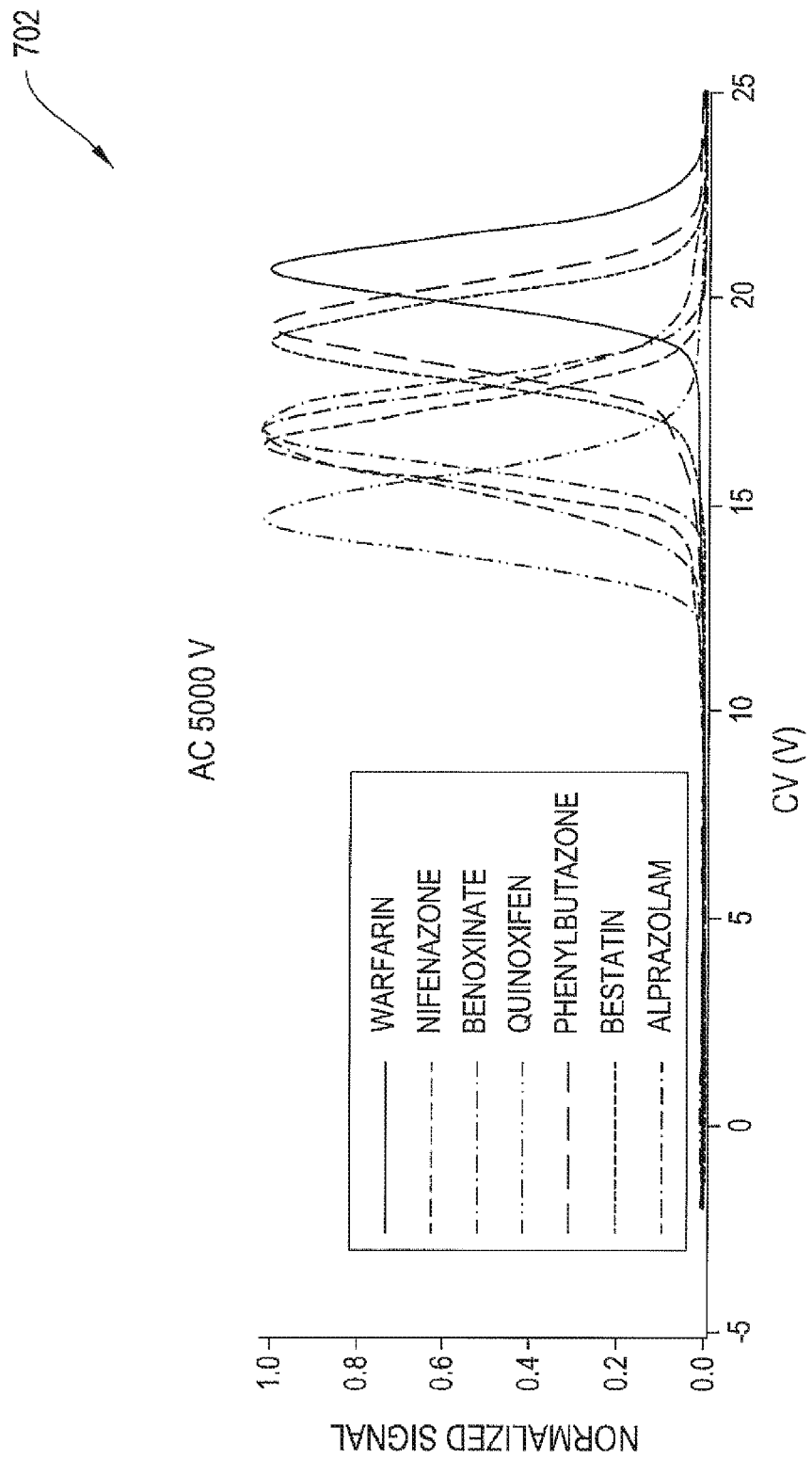
Figure 7B:
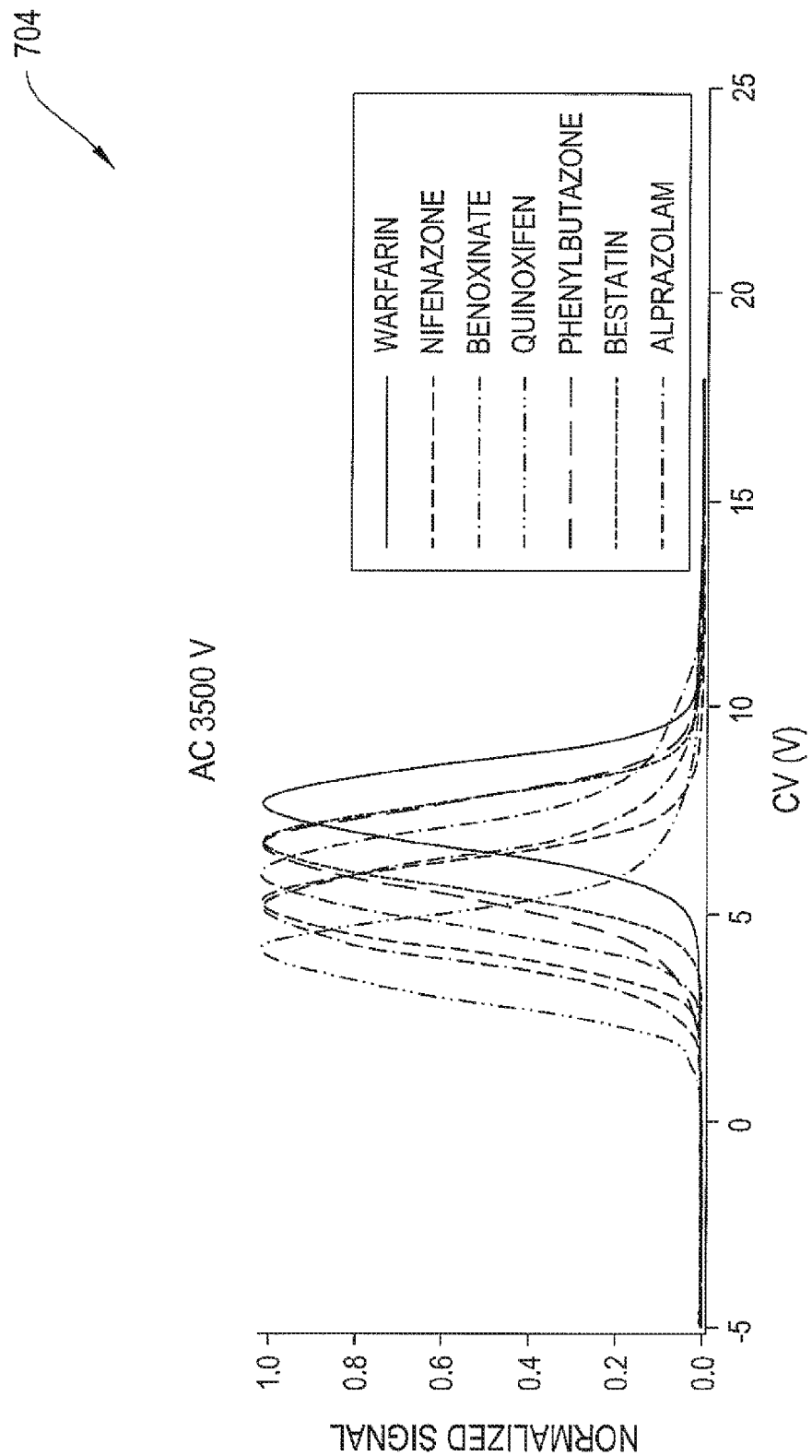
Figure 7C:
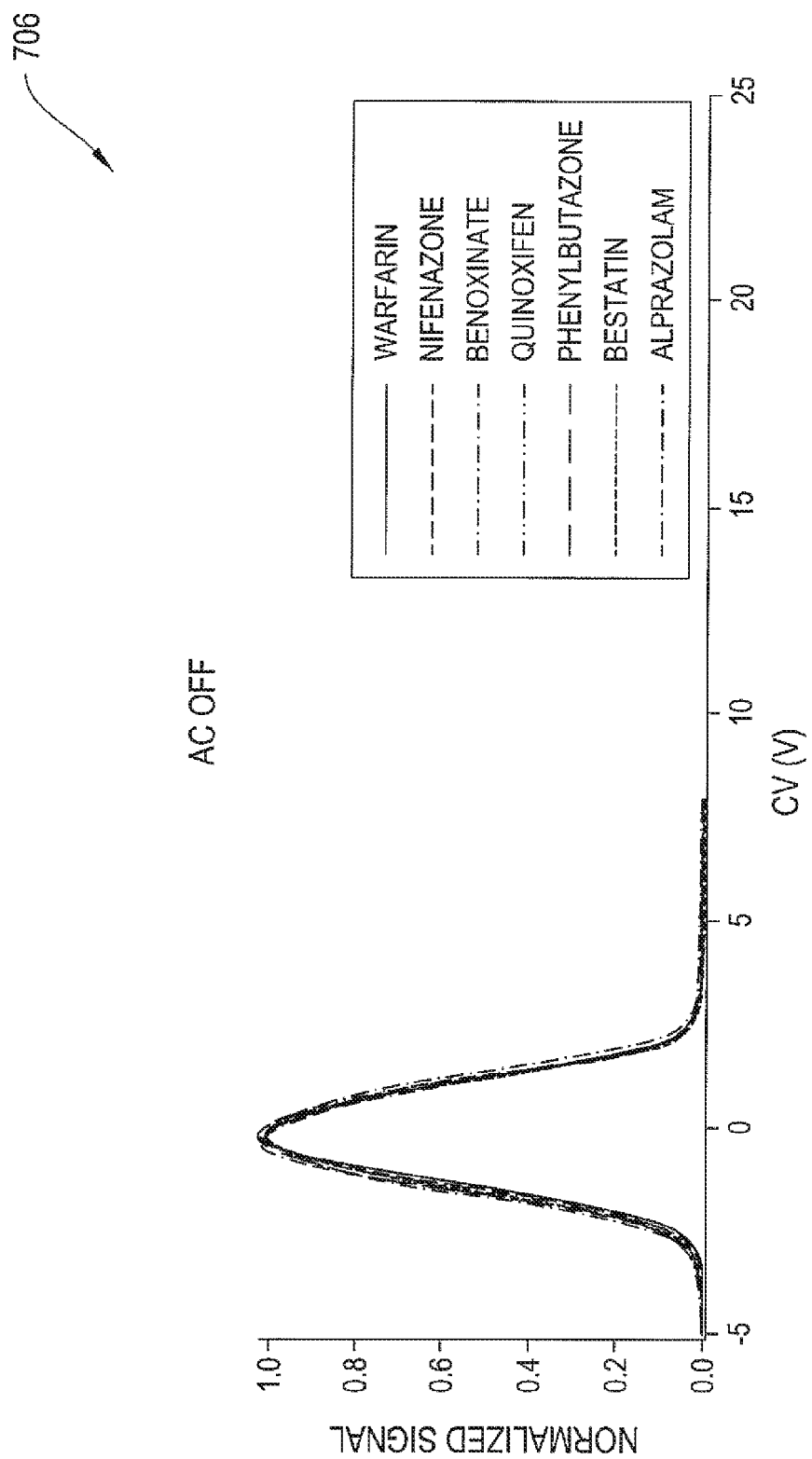
Figure 8:
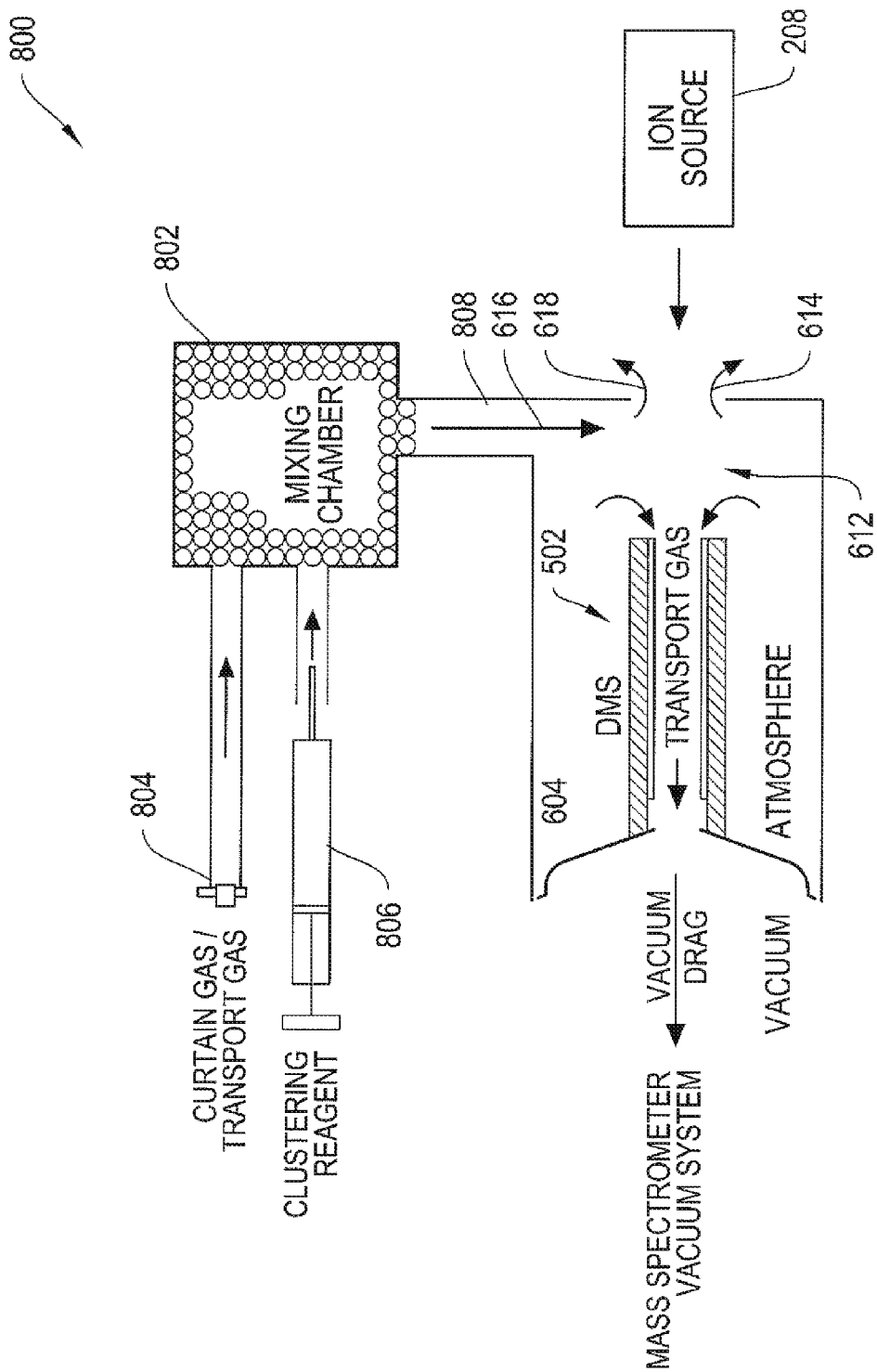
Figure 9:
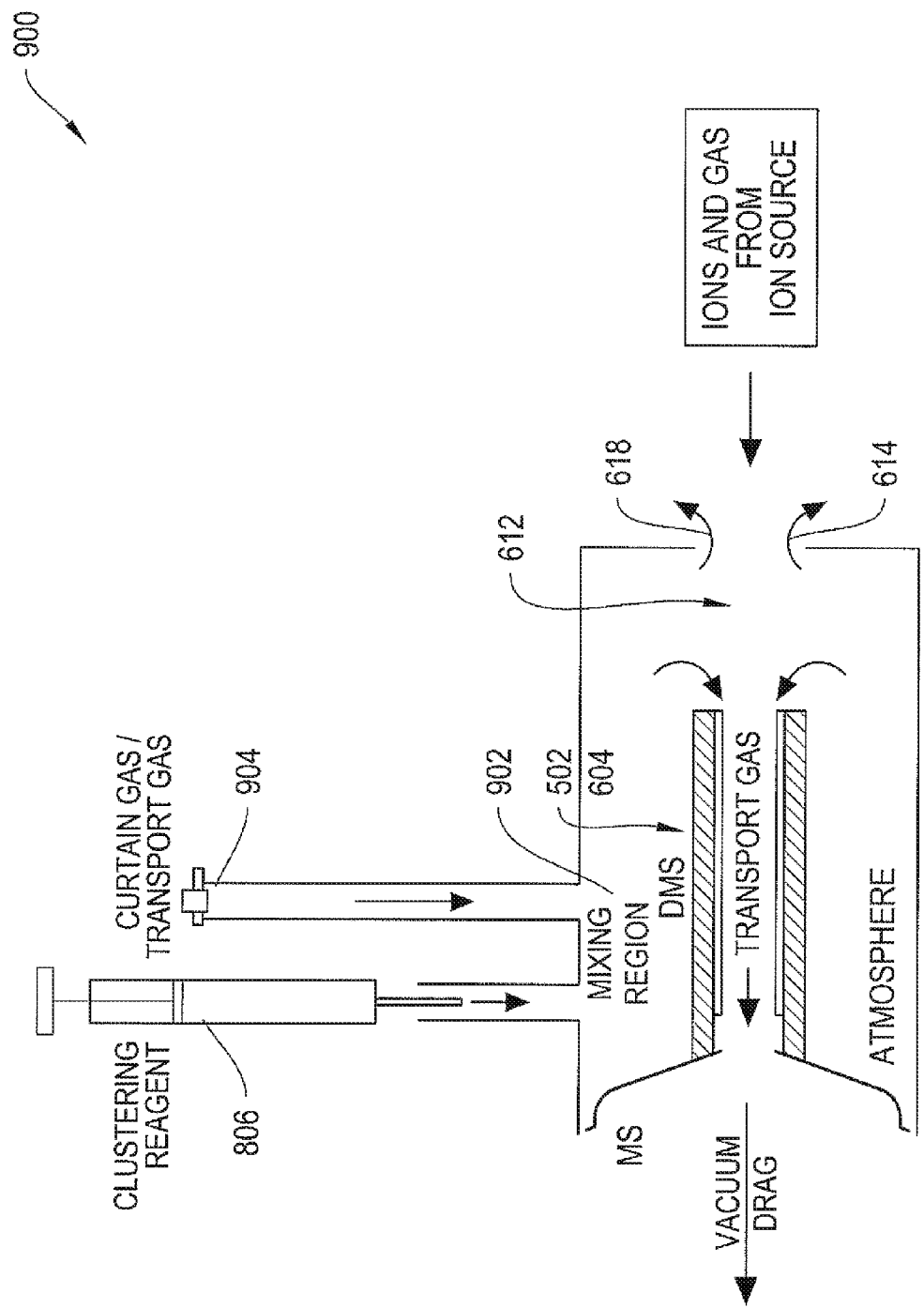
Figure 10:
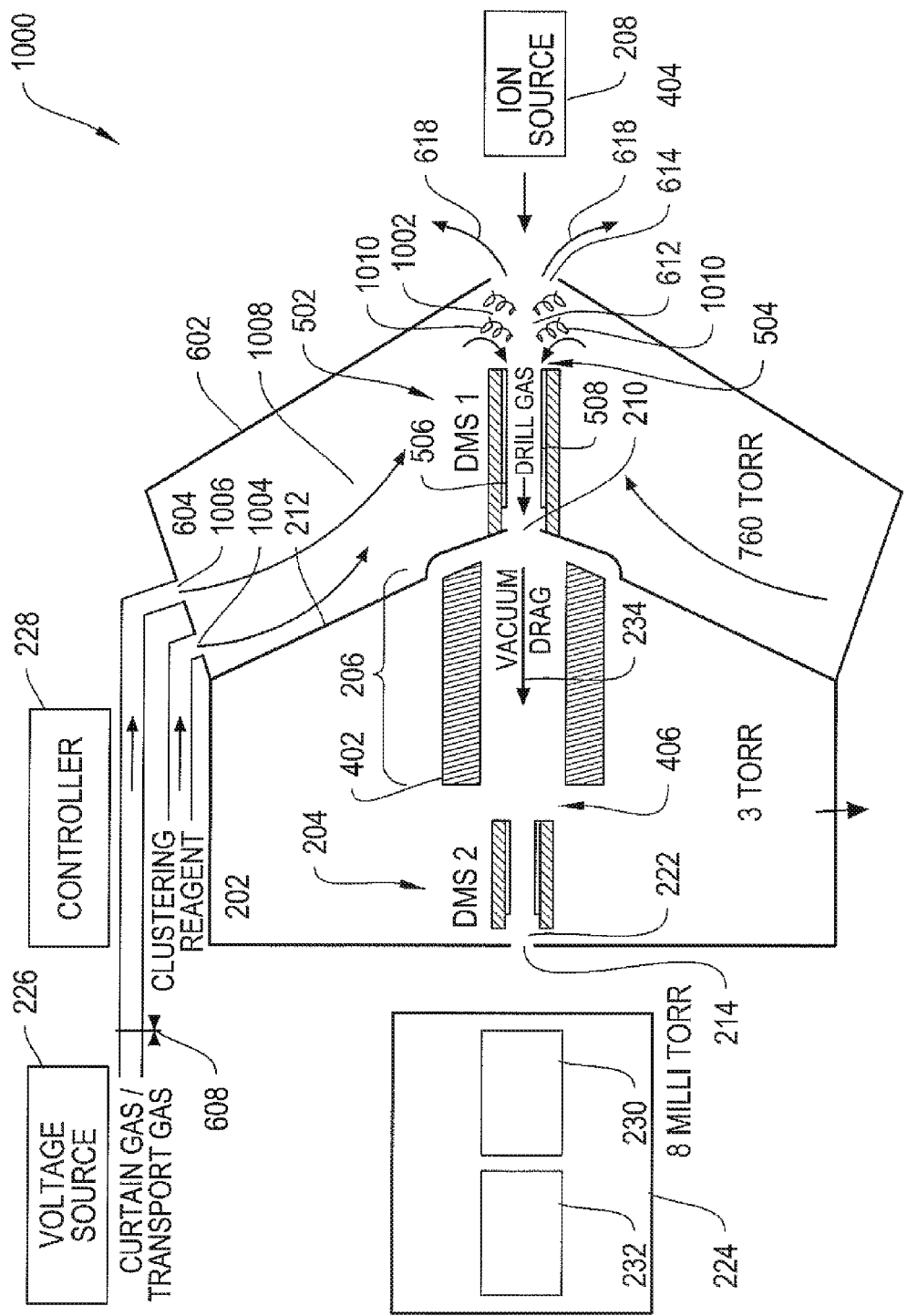
Figure 11:
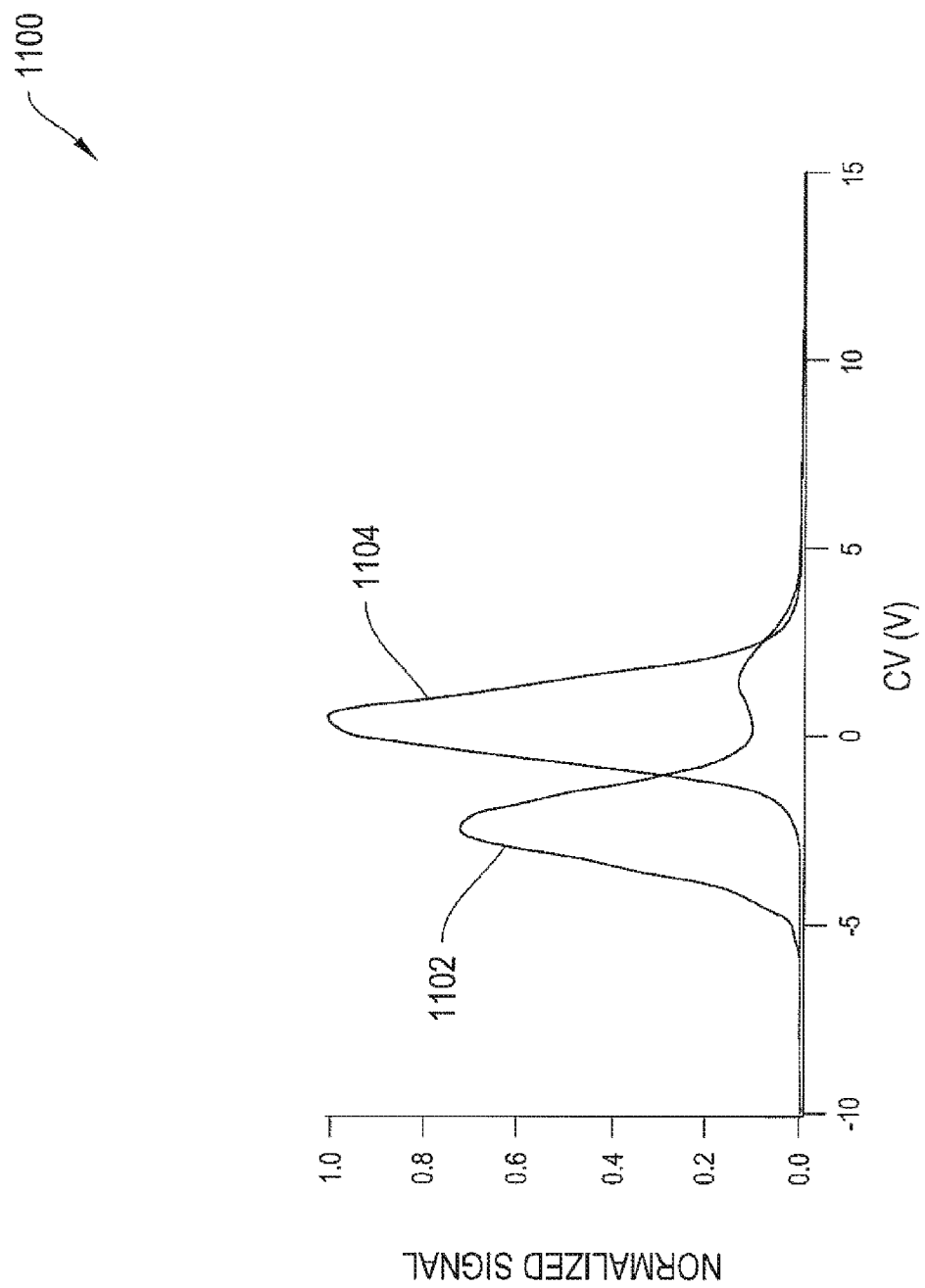
Figure 12:
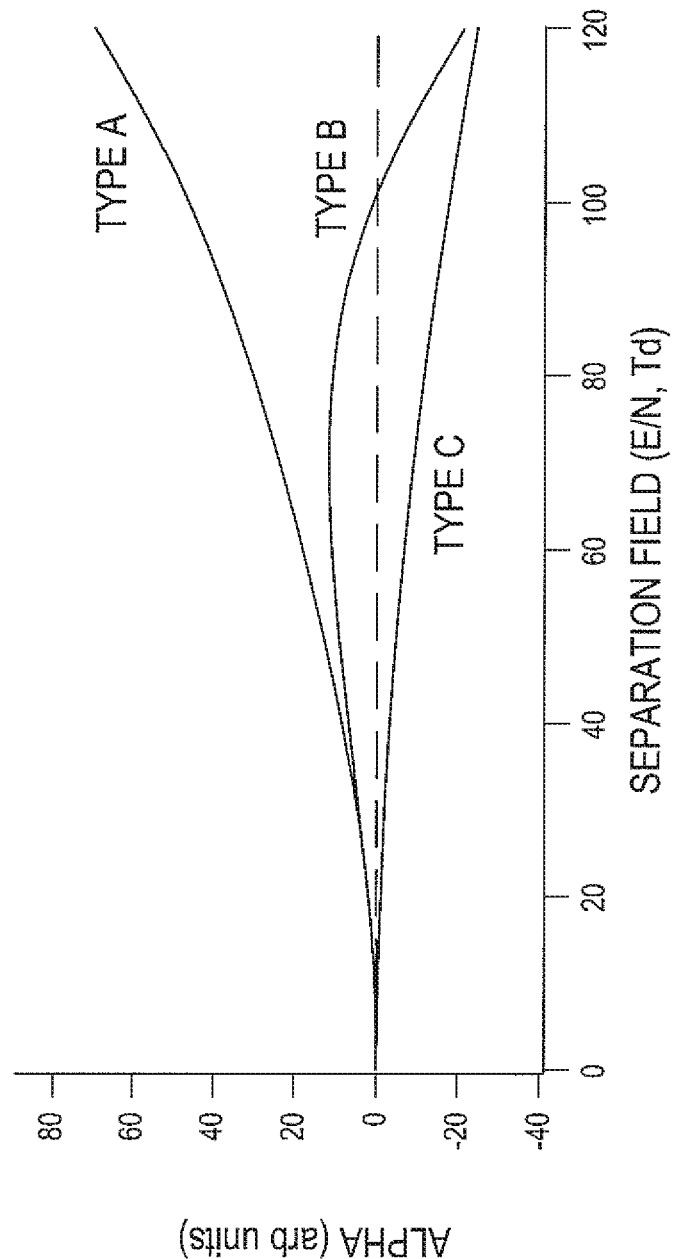
Figure 13:
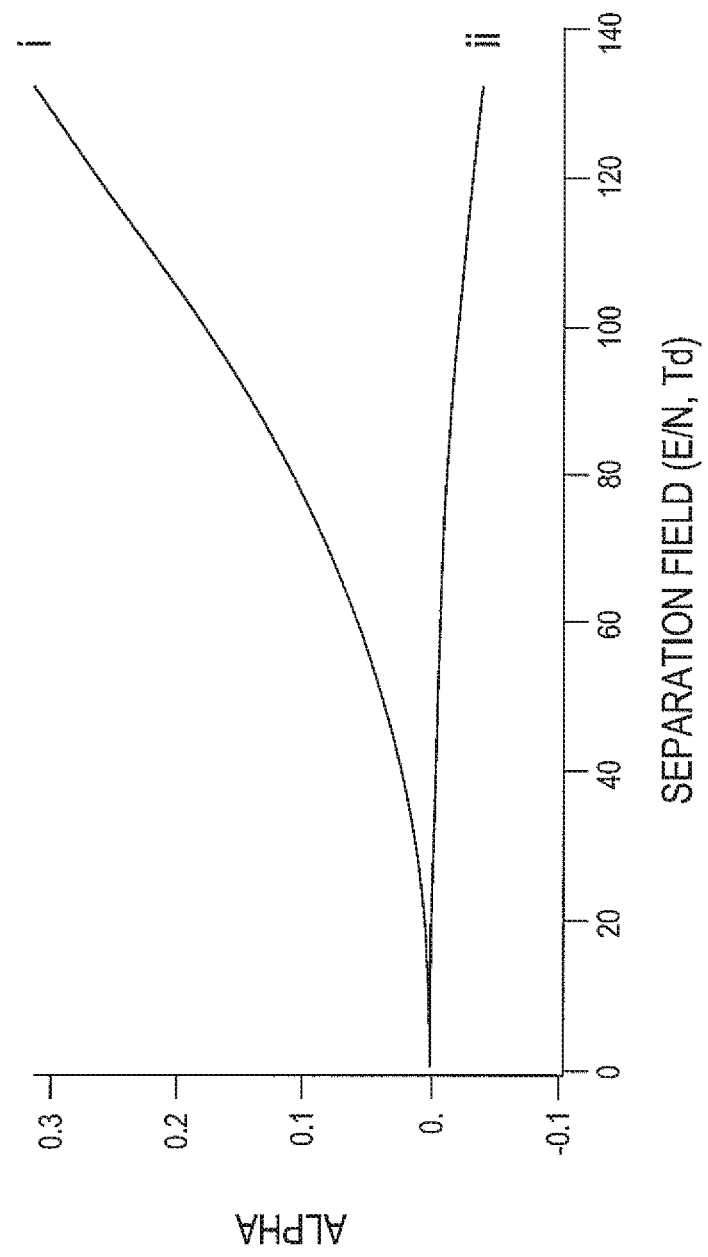
Figure 14A:
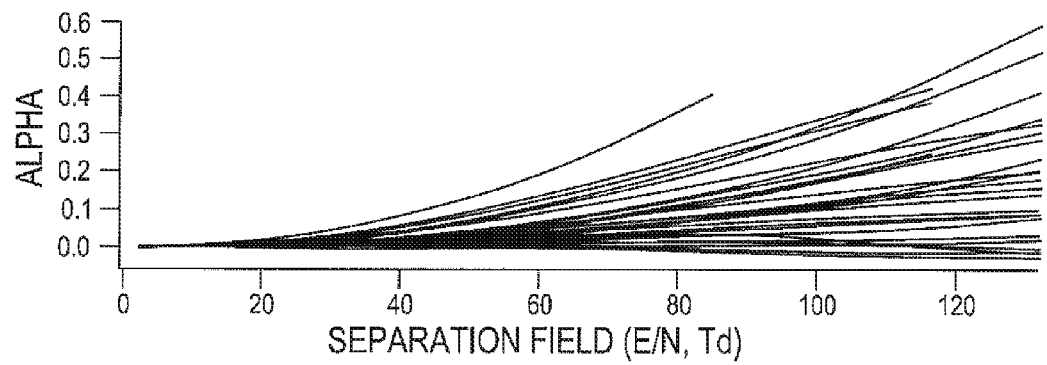
Figure 14B:
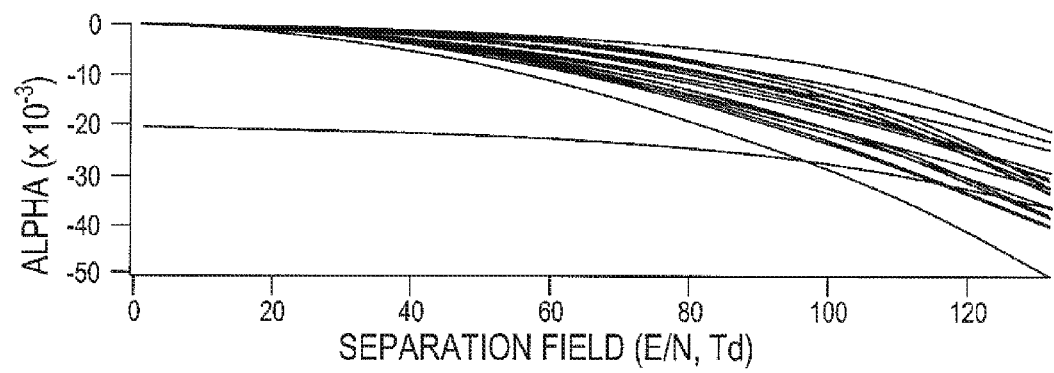
Figure 14C:
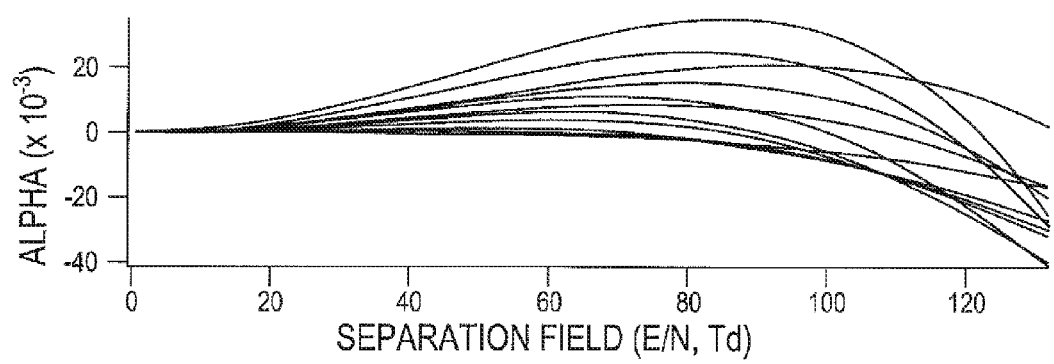
Figure 15A:
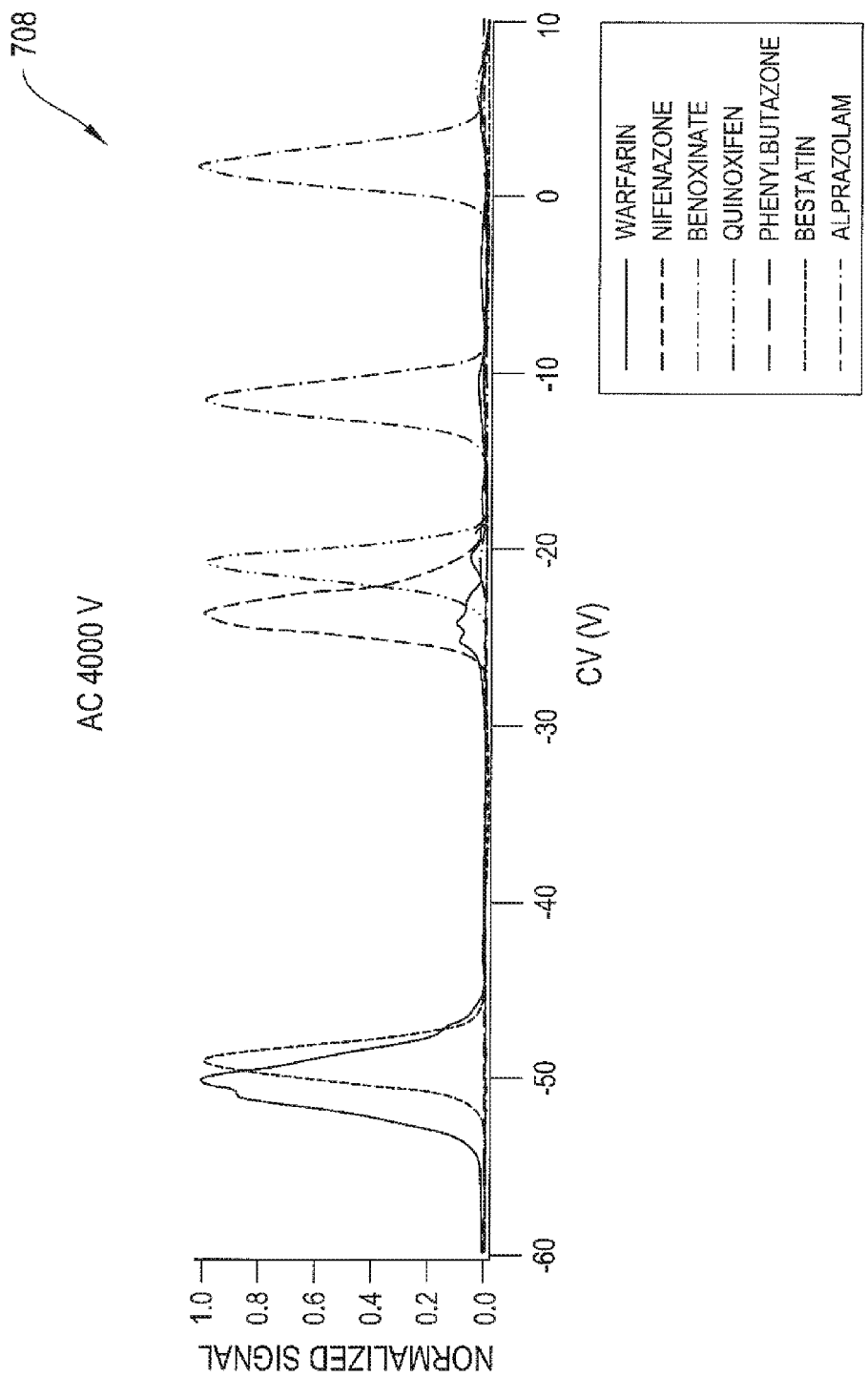
Figure 15B:
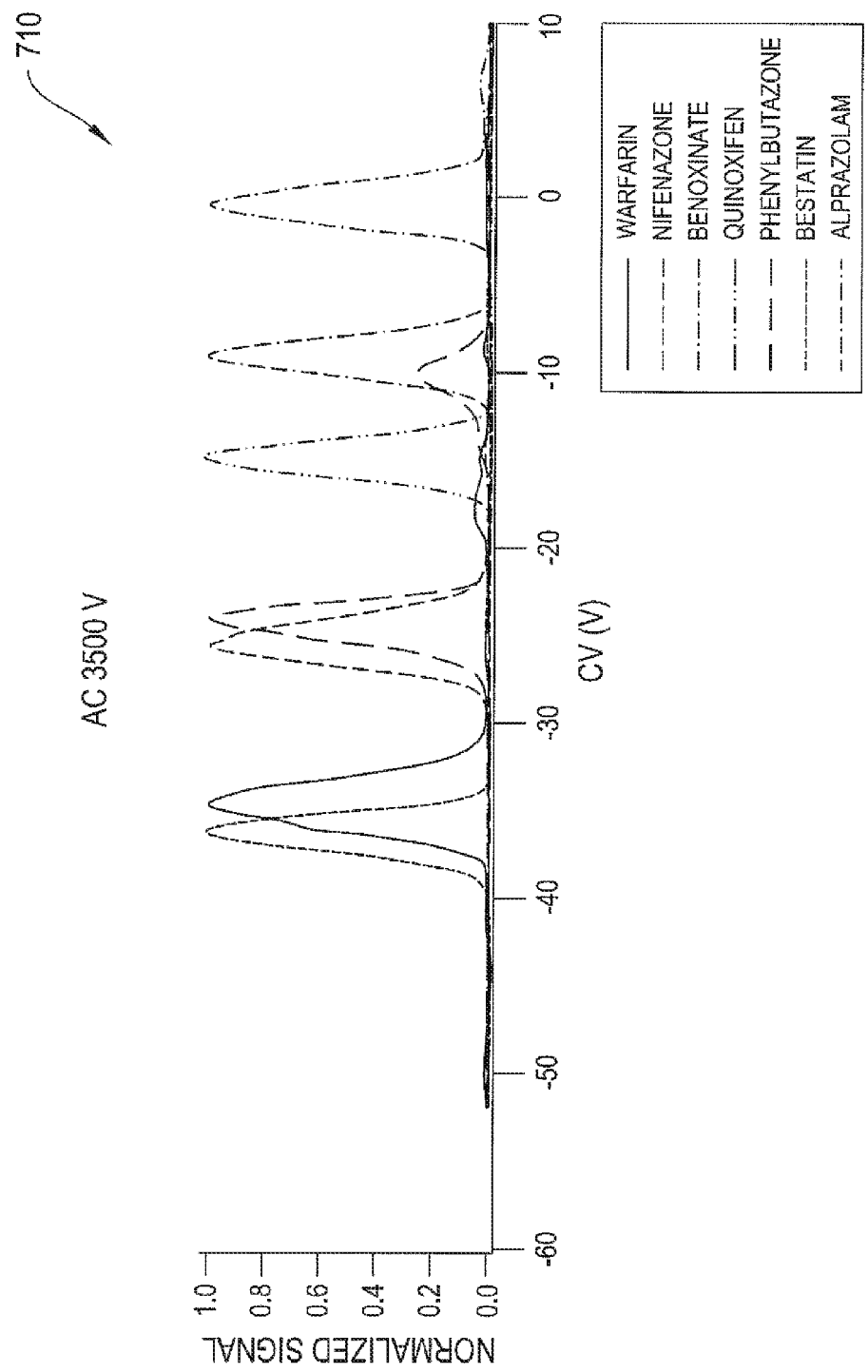
Figure 15C:
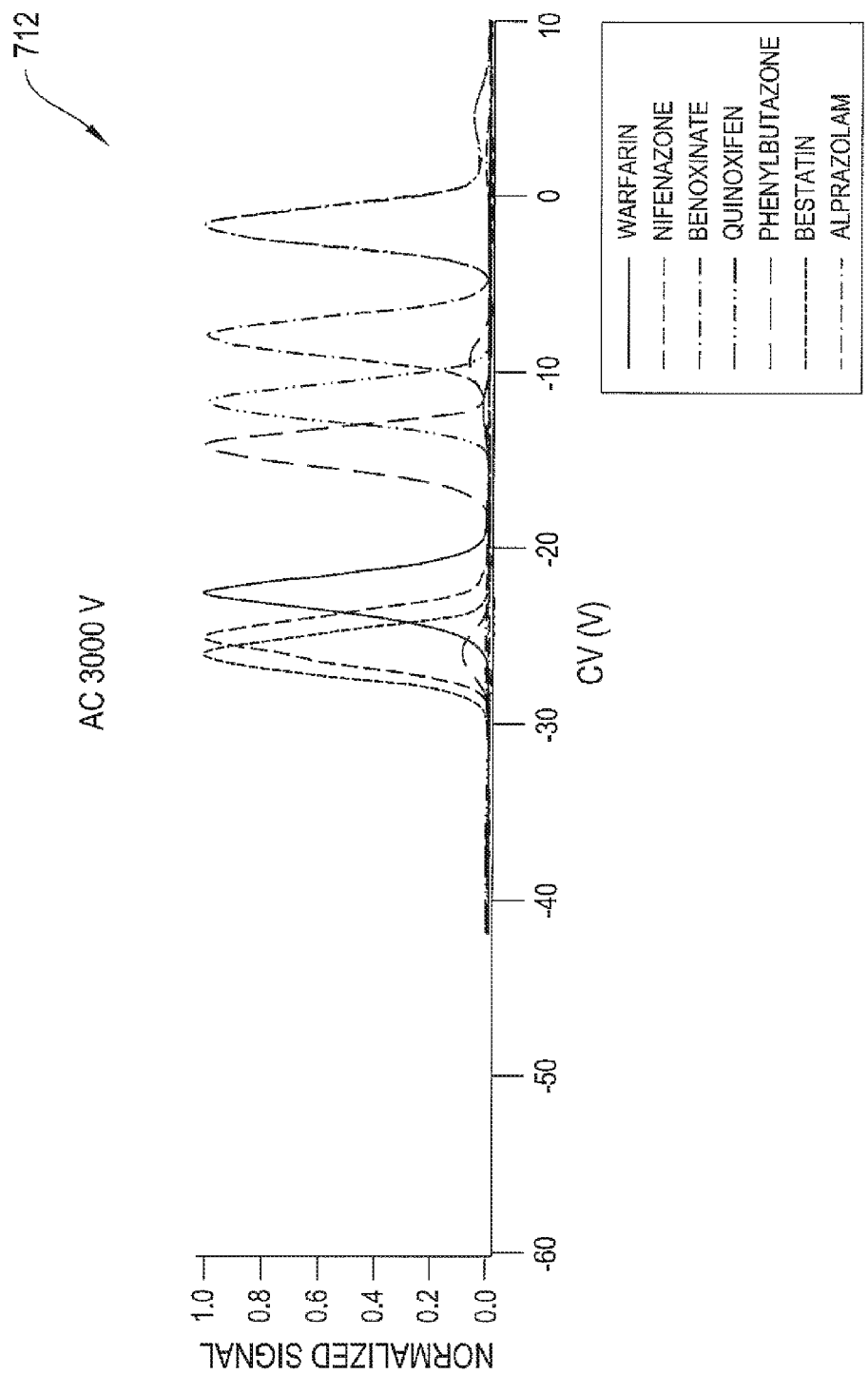
Figure 15D:
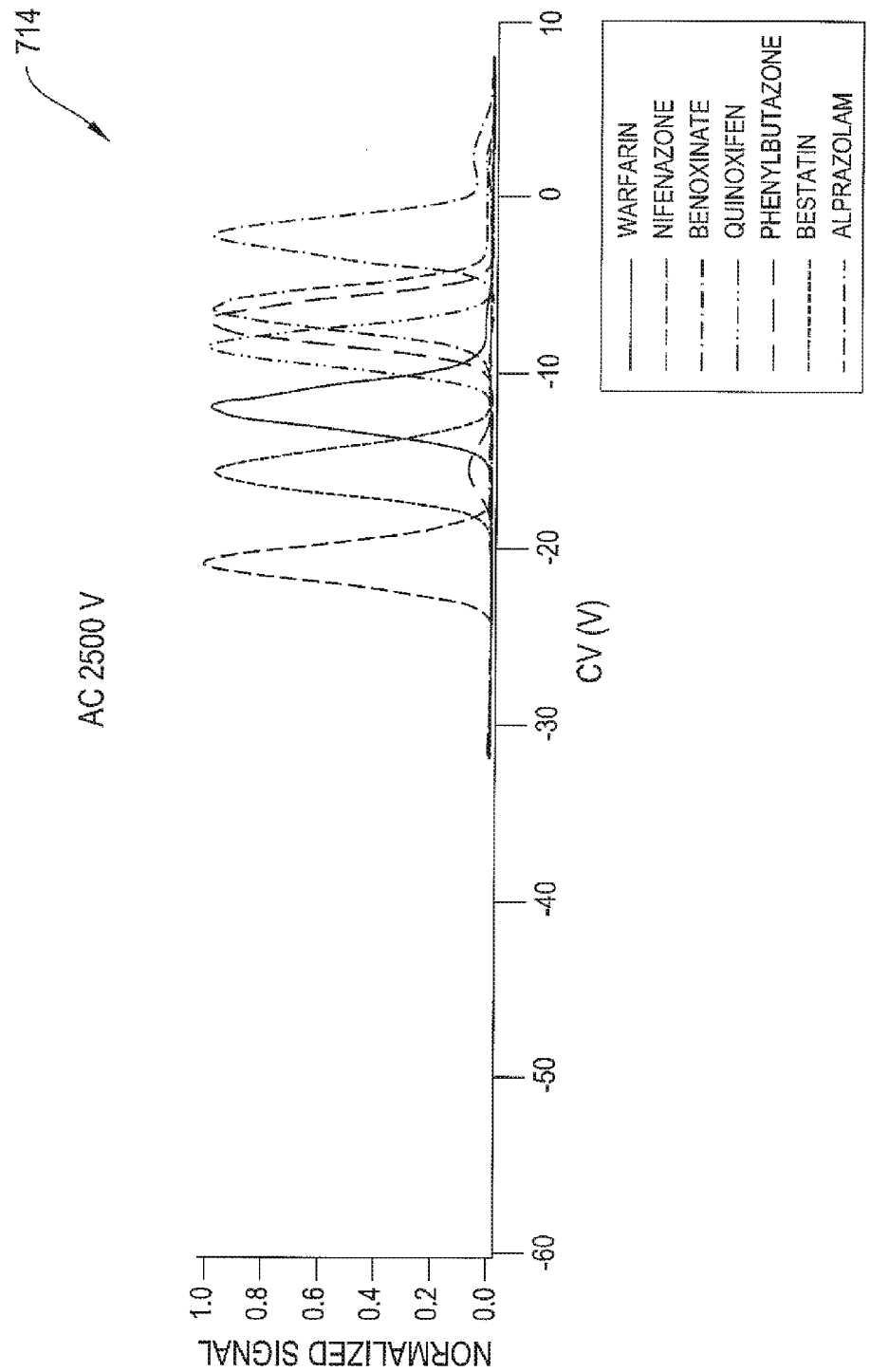
Figure 15E:
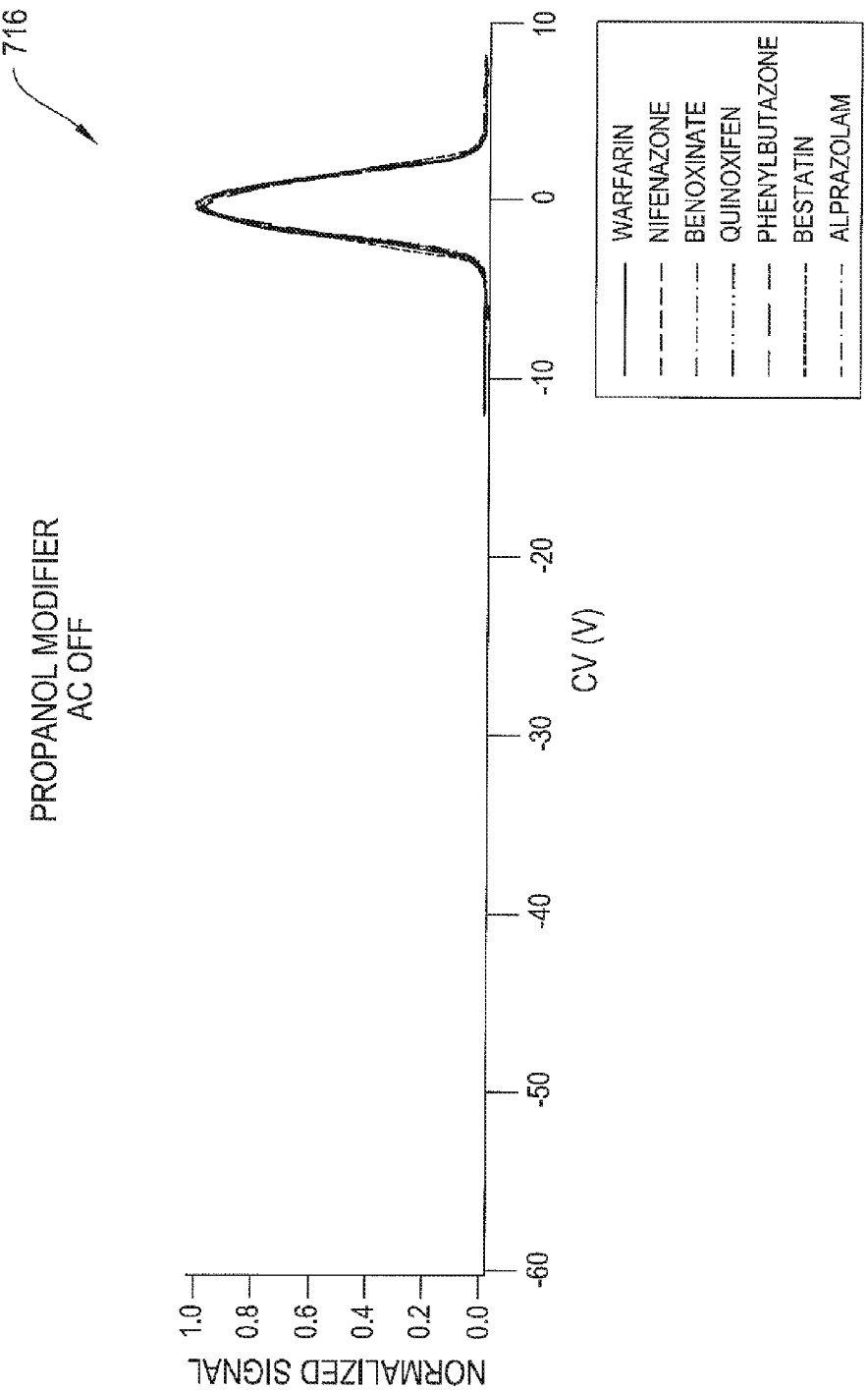

FIGS. 7A-C includes plots of normalized ion intensity peaks in a DMS without reagent modifiers at various Vrf settings;

FIG. 8 shows a diagram of dopant introduction system via a mixing chamber according to an illustrative embodiment of the invention;

FIG. 9 shows a diagram of an alternative dopant introduction system according to an illustrative embodiment of the invention;

FIG. 10 shows a diagram of a mass analysis system as in FIG. 6 with a turbulent heated region according to an illustrative embodiment of the invention; and FIG. 11 is a graph including plots of normalized ion intensity vs. compensation voltage when the inlet to the atmospheric pressure DMS is heated and not heated respectively;

FIG. 12 is a graph of the of alpha behavior for type A, B, and C ion mobility behavior;

FIG. 13 is a graph showing the dramatic changes that occur in the alpha function for a sample of norfentanyl with inert transport gases and the inclusion of a clustering modifier; and FIGS. 14A-C includes a series of graphs showing alpha function data for 36 compounds under different conditions.

FIGS. 15A-E includes plots of normalized ion intensity peaks in a DMS with reagent modifiers introduced at various Vrf settings.

DESCRIPTION OF VARIOUS EMBODIMENTS

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

A common problem with electrospray ionization sources is that they typically produce heterogeneous ion clusters that can adversely affect the resolution of ion analyzer systems. Clustering of ions and neutral gas phase molecules typically results from ionization at atmospheric pressure. Ions generated during the electrospray process are a combination of bare molecular ions and ions clustered or contained in small droplets of the electrospray solvent. The relative proportion of ions, ion-clusters, and charged droplets is highly dependent on the degree to which the charged nebulized liquid is desolvated.

When a mobility based analyzer, such as a DMS, is used with an electrospray ionization source, the extent of the production of these heterogeneous cluster ion populations is related to mobile phase introduction flow rate. When the mobile phase flow rates extend into the hundreds of microliters per minute range, a large proportion of the ions produced by the ion evaporation process are created as clusters and small droplets of widely varying composition. Cluster ion populations formed in this way are highly heterogeneous and different from the relatively homogeneous cluster ion populations formed in the gas phase during the interaction of an ion with the background transport gas.

A particular ion can exist in a wide variety of different clustered states covering a broad distribution of molecular weights and chemical compositions. This occurs whether or not high desolvation temperatures are used to evaporate the pneumatically nebulized electrospray, although the problem is exacerbated at low temperatures. A mobility based analyzer such as a DMS, operating at atmospheric pressure, can separate the components of the distribution. However, the sensitivity for the targeted analyte, as detected by, for example, a MS, will be reduced in addition to the mobility resolution and peak capacity. Under conditions of incomplete electrospray desolvation, heterogeneous clusters of different sizes and compositions may be present in addition to small droplets. These clusters will show a much greater range of differential mobility values and a correspondingly greater peak width.

Electrospray sources operating at liquid flows in the nano-liter to low microliter per minute range produce fewer clusters and, depending on the analyte and solvent chemistry, will often produce unclustered molecular ions prior to the vacuum inlet of an MS. This is apparent when Vc scans of an electrosprayed solution of a standard compound are done at high and low liquid flow rates. The apparent loss of resolution as the flow rate is raised can be attributed to the formation of increasingly heterogeneous analyte/cluster ion populations and possibly the persistence of small droplets within the mobility based analyzer.

One approach to addressing the resolution problem at relatively high flow rates is by dissociating ion clusters prior to mobility based filtering. In certain embodiments, a dissociation region is established before ion mobility based filtering. In some embodiments, a low pressure DMS is used to filter ions based on the rigid sphere collision (or scattering) model after dissociation of ion clusters. In other embodiments, where ion mobility based filter of ion clusters is preferred, an atmospheric pressure DMS provides ion mobility based filter based on the clusterization model. In further embodiments, an ion analyzer system includes both a low pressure DMS and atmospheric pressure DMS that combines the advantages of ion mobility based filtering using both models. Further details regarding the rigid sphere collision and clustering models are provided later herein with respect to FIG. 12.

Figure 2:
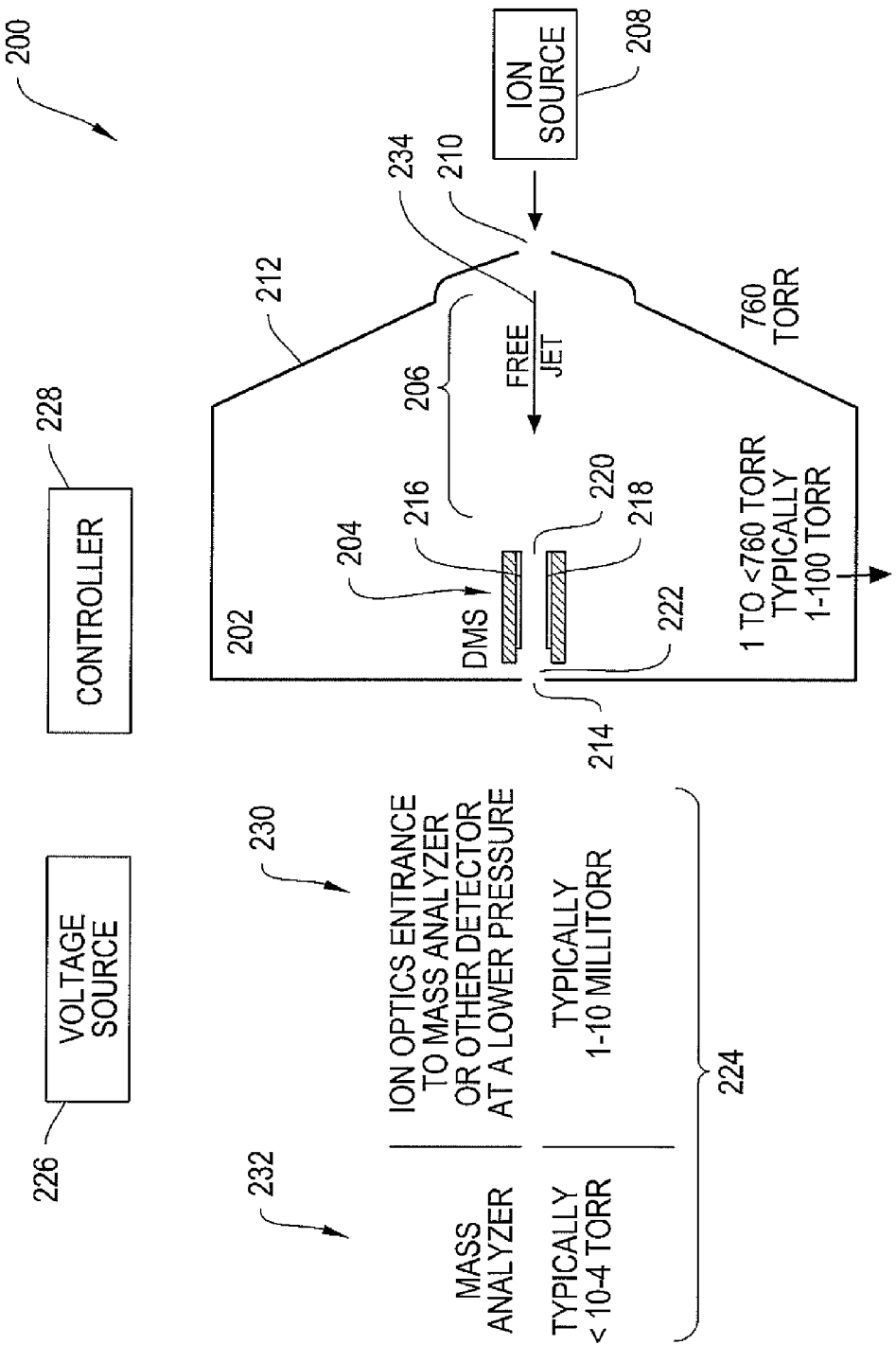
FIG. 2 shows a diagram of a mass analysis system with a vacuum chamber including a DMS and collision region according to an illustrative embodiment of the invention.

FIG. 2 shows a diagram of a mass analysis system 200 with a vacuum chamber 202 including a DMS 204 and dissociation region 206 according to an illustrative embodiment of the invention. The system 200 also includes an ion source 208, vacuum chamber inlet and/or orifice 210, vacuum plate 212, an outlet orifice 214, a mass spectrometer 224, a voltage source 226, and controller 228. The DMS 204 includes filter electrodes 216 and 218, a DMS inlet 220, and DMS outlet 222. The mass spectrometer 224 includes an ion optics assembly 230 and mass analyzer 232, and ion detector (not shown). In certain embodiments, the dissociation region 206 includes at least one of a collision region, declustering region, desolvation region, and gas expansion region.

The vacuum chamber inlet 210 is in communication with the ion source 208 and may include an orifice, a pipe, a heated capillary, a resistive capillary, or any suitable sample inlet configuration known to one of ordinary skill in the art. The vacuum chamber inlet 210 may be part of a sample inlet system that includes components such as a source extension ring or the like to facilitate ion introduction into the vacuum chamber 202 via the sample inlet 210. The ion source 208 may be integrated with the vacuum chamber inlet 210 or an inlet system or, alternatively, may be separate from the inlet system. The ion source 208 may be any suitable ion source known to one of skill in the art. For example, the ion source 208 may include an electrospray ionization source with the ability to generate ions from a sample analyte dissolved in solution. Other example arrangements of the ion source 208 may include an atmospheric pressure chemical ionization (APCI), atmospheric pressure photo-ionization (APPI), direct analysis in real time (DART), desorption electrospray (DESI), atmospheric pressure matrix-assisted laser desorption ionization (AP MALDI), liquid chromatography (LC) column, gas chromatography (GC) column, multimode ionization sources, surface analysis sources, or configurations with multiple inlet systems and/or sources.

The vacuum chamber 202, in certain embodiments, is configured to include a low pressure dissociation region 206 and/or declustering region located upstream of the DMS 204. The low pressure dissociation region 206 may be configured to accelerate sample ions from the vacuum chamber inlet 210 within a free jet expansion. The vacuum chamber 202 may be defined or bounded by a vacuum plate 212 and/or housing. Sample ions travel through the inlet 210, where a vacuum expansion occurs, as a result of the pressure differential on either side of the inlet 210. The low pressure dissociation region 206 may include a pressure gradient along the sample ion flow path 234 whereby the pressure is reduced from about atmospheric pressure in proximity to the vacuum chamber inlet 210 to a set pressure below atmospheric pressure in proximity to the DMS inlet 220. The pressure in proximity to the DMS inlet may be from about 1 Torr to less than atmospheric pressure (e.g., 760 Torr). In some embodiments, the DMS can operate at about 50 to about 760 Torr. In certain configurations, the DMS can operate from about 200 to about 500 Torr. In certain configurations, the DMS can operate at about 200 Torr. In some embodiments, the pressure may be from about 1 Torr to less than or equal to about 100 Torr. In certain circumstances, the sample ions are accelerated in the low pressure dissociation region 206 with voltage and collided into a background gas to effect declustering and/or fragmentation prior to delivery of the sample ions to the DMS 204.

DMS residence time and gap height can be affected by the operating pressure, with lower pressures requiring wider gaps and longer residence time. For example, Table 1 below shows typical gap widths and residence times for the DMS at different operating pressures. Long residence times can limit sample throughput, therefore it may be advantageous to operate the DMS in the about 100 to about 760 Torr pressure regime.

TABLE 1

| Pressure (Torr) | Gap Height (mm) | Residence Time (ms) |
| --- | --- | --- |
| 2.5 | 240 | 1579 |
| 10 | 60 | 385 |
| 20 | 30 | 193 |
| 50 | 15 | 93 |
| 100 | 7 | 44 |
| 200 | 3.5 | 22 |
| 300 | 2.1 | 13.5 |
| 500 | 1.3 | 8.4 |
| 760 | 0.8 | 5.1 |

The DMS 204, also referred to as a field asymmetric ion mobility spectrometer (FAIMS), may include filter electrodes 216 and 218 that are formed and/or configured as parallel plates, curved plates, concentric rings/surface, and the like. The DMS 204 may include a plurality of filter electrode pairs. The filter electrodes 216 and 218 may be formed on or connected to insulating surfaces or components. The DMS 204 may have form factor including a generally planar, circular, concentric, and/or curved structure. The voltage source 226 applies RF and DC voltages to at least one of the filter electrodes 216 and 218 to generate an electric field to enable sample ion filtering based on the mobility characteristics of the sample ion species while traveling through the DMS 204. The DC voltage is referred to as the compensation voltage, Vc, because the Vc may be adjusted to select a desired ion species to pass through the DMS 204. The controller 228 may control the voltage 226 so that the voltage source 226 sweeps Vc over a range of DC voltages to produce a ionogram or spectrum of sample ion species that are allowed to pass through the DMS 204. It will be appreciated that other ion mobility based separation devices and/or filters may be used in the system 200 such as, without limitation, an Ion Mobility Spectrometry (IMS), a Differential Mobility Analyzer (DMA), a hybrid ion mobility based analyzer, a high-field/low-field filter, and the like. The DMS assembly 204 may be mounted so as to provide vacuum seal to exit aperture 214 so that gas drag through aperture 214 establishes a laminar gas flow through the DMS 204. Additionally, DC potentials may be provided to electrodes 216 and/or 218 to adjust the DC offset potential between DMS 204 and aperture 214 to optimize transmission.

The ion optics assembly 230 may use RE fields to focus the sample ions from the orifice 214 on to an ion optical path and direct the ions toward the mass analyzer 232. It will be appreciated that the ion optics assembly 230 used in system 200 may be made up of any ion optics known to one of skill in the art, such as, without limitation, a multipole array, a ring guide, a resistive ion guide, an ion funnel, a traveling wave ion guide, or the like. In certain embodiments, the ion optics assembly is operated at a pressure in the range of about 1-10 millitorr.

In some embodiments, the ion optics assembly 230 is connected with the mass analyzer 232 to enable sample ions to travel via ion optical path to mass analyzer 232 where the ions are separated based on their mass-to-charge ratios (m/z) and detected. The detected ion data may be stored in memory and analyzed by a processor or computer software. In certain embodiments, the controller 228 includes a processor and memory or data storage. The controller 228 may also control the operation of the mass analyzer 232. The mass analyzer 232 may function as at least one of a linear ion trap and a quadrupole analyzer, time-of-flight MS, or include multiple mass analyzers. In certain embodiments, the ion optics assembly may include the Q0 RF ion guide or any like ion guide. An ion guide may be used to capture and focus sample ions from the orifice 214 using a combination of gas dynamics and radio frequency fields. An ion guide, such as Q0, may then transfer sample ions from the orifice 214 to subsequent ion optics or the mass analyzer 232.

The API 5000™ system, manufactured by AB Sciex is one type of exemplary mass spectrometer 224 that may be utilized by the mass analysis system 200. Such a mass spectrometer typically includes instrumental optics, a mass analyzer, curtain plate and orifice. Instrumental optics comprise a QJET® RF ion guide and Q0 RF ion guide separated by an IQ0 lens. The QJET® RF ion guide is used to capture and focus ions using a combination of gas dynamics and radio frequency fields. The QJET® transfers ions from the orifice to subsequent ion optics such as the Q0 RF ion guide. The Q0 RF ion guide transports ions through an intermediate pressure region (e.g., at about ~6 mTorr) and delivers ions through an IQ1 lens to a high vacuum chamber containing a mass analyzer. The mass analyzer region comprises a Q1 quadrupole analyzer, Q2 quadrupole collision cell, Q3 quadrupole analyzer and CEM detector.

The instrumental optics comprising an ion guide and/or Q0 RF ion guide are an example of optics that can be used in ion optics assembly 230 of FIG. 2. However, in some embodiments the elements can be used individually, in combination with other types of ion optics, or not used in mass spectrometer system 224 at all. In some instances, a Q0 ion guide may be capacitively coupled to either the Q1 or Q3 quadrupole. In some configurations, the ion optics and mass analyzer can include one or more pressure regions, separated by apertures, operating at various range of pressures. For example, the first region may be set at 2.5 Torr, Q0 set at 6 mTorr and mass analyzer, comprising Q1, Q2 and Q3, may be set at $10^{-5}$ Torr. It will be apparent to those of skill in the art that Q2 can comprises a collision cell for fragmenting ions, and the gas pressure within the Q2 cell may be substantially higher than the pressure in Q1 and Q3 of the API 5000™ device.

In some embodiments that require short residence times, the first region can be set to 50 to 760 Torr, the second QJET® region can be set to 2.5 Torr, Q0 can be set to 6 mTorr, and the mass analyzer comprising Q1, Q2, and Q3 can be set to $10^{-5}$ Torr.

In certain embodiments, the controller 220 includes a processor that enables the control of the various components of the mass analysis system 200 including the DMS 204, the voltage source 226, the ion source 208, the mass spectrometer 224, and, more particularly, the ion optics 230, and mass analyzer 232. The controller may include a user interface, network interface, and data storage. The processor may include an interface with a memory having software and/or hardware code configured to enable the control of the system 200. The controller 228 may include program code embedded on program media to enable the processor to perform instructions to effect control of the system 200 and/or analysis or processing of data acquired from the operation of the system 200.

The mass spectrometer 224 may include at least one electrode, e.g., a linear accelerator (LINAC) in close proximity to the ion optics assembly 230. The electrode or electrodes may be used for accelerating ions through an RF multipole or expelling residual ions from the RF multipole. The voltage source 226 (e.g., power supply) may be connected to and apply a DC potential to the electrode(s), causing the electrodes to generate an electric field to axially expel ions, including residual ions, out of the ion optics assembly 230, or out of another component of the system 200. The electrodes may also accelerate ions to reduce the residence time within the ion optics assembly 230 and, thereby, reduce or substantially eliminate ion beam spreading.

The voltage source 226 may include an RF/DC auxiliary alternating current (AC) power supply that supplies RF and/or DC signals, and/or an auxiliary AC signal to a quadrupole rod set of the mass analyzer 232. The system 200 may include a shortened quadrupole rod set, which can act as Brubaker lenses, adjacent to the mass analyzer 232 or other component of the system 200.

In certain embodiments, the mass spectrometer 224 may include a collision cell having an inert gas (for example, helium, nitrogen, argon, or the like) that can be pumped into the collision cell to initiate collision induced dissociation (CID) of ions. Ions in a collision cell, such as parent ions, can collide with gas molecules and break into fragments, referred to as daughter ions. In certain embodiments, when a component of the mass spectrometer 224 functions in an ion trap mode, an RF power supply can be used to create an electric field within a quadrupole rod set of the ion trap. By changing the amplitude and waveform of the applied field, ions of a selected m/z can be trapped within the quadrupole rod set. In some configurations, the mass analysis system 200 performs Multiple reaction monitoring (MRM).

Figure 3:
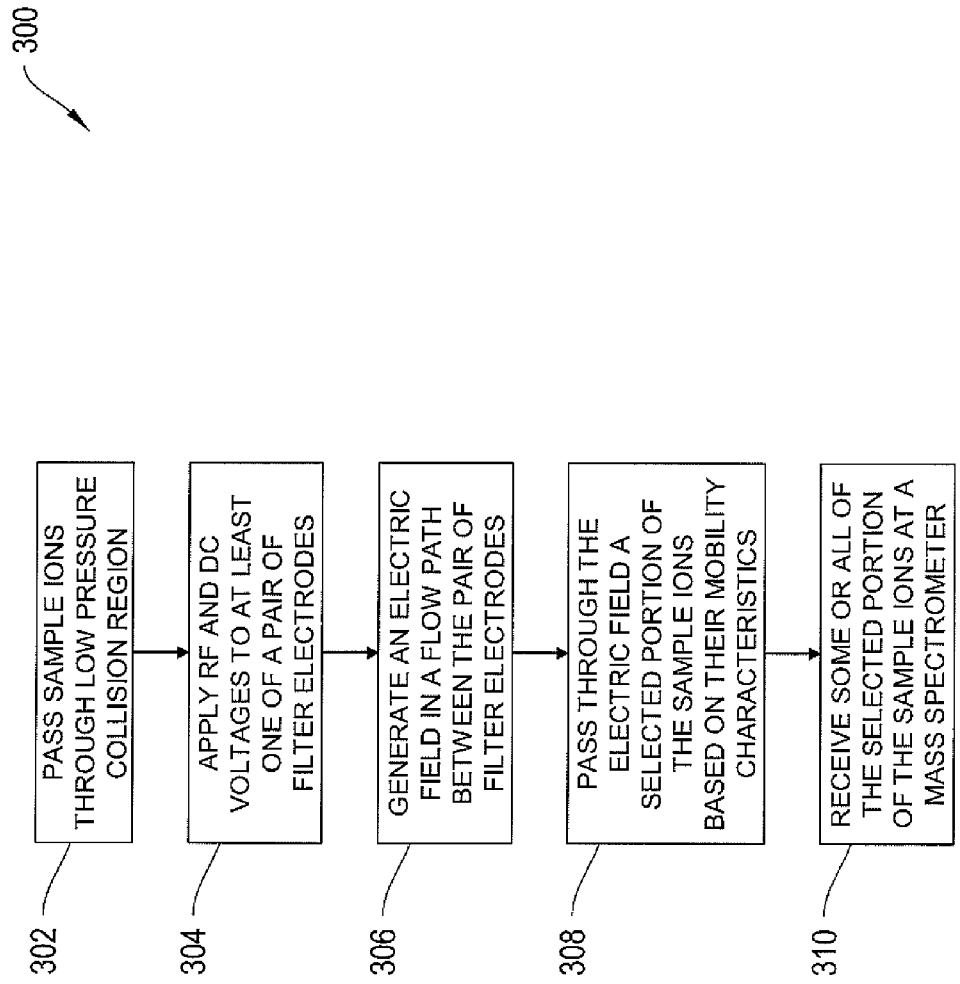
FIG. 3 is a flow diagram of a process for analyzing ions using the system of FIG. 2 according to an illustrative embodiment of the invention.

FIG. 3 is a flow diagram of a process 300 for analyzing ions using the system 200 of FIG. 2 according to an illustrative embodiment of the invention. In one embodiment, the ion source 208 includes an electrospray ionization source that delivers sample ions from a solution to the vacuum inlet 210. As discussed previously, electrospray ionization, particularly at high flow rates, can produce heterogeneous ions which are undesirable. One approach to mitigating the adverse effects of heterogeneous clusters is to dissociate the ion clusters before ion mobility based filtering.

The pressure at the ion source 208 may be at about atmospheric pressure, while the pressure inside the vacuum chamber may be at a pressure less that atmospheric pressure. Thus, the pressure differential across the vacuum inlet 210 can create a free jet within the vacuum chamber 202 to pass and accelerate sample ions through the low pressure collision region 206 along the flow path 234 toward the DMS inlet (Step 302). The arrangement and use of the low pressure collision region 206 advantageously enables declustering of the heterogeneous sample/solvent cluster ions because the sample ion clusters in the wet spray from the ion source 208 are accelerated within the free jet expansion of the low pressure collision region 206. By declustering and/or desolvating the sample ions in the low pressure collision region 206 before entry into the DMS 204, the sensitivity of the system 200 is advantageously improved because the DMS 204 is allowed to filter the desired sample ions, as opposed to filtering clusters.

As discussed previously, when creating clusters in the gas phase, as opposed to during electrospray ionization, clusters are homogeneous and, therefore, form well-defined structures and resulting well-defined detection peaks. Unlike heterogeneous ion clusters, homogeneous cluster ion populations are formed in the gas phase during the interaction of an ion with the background transport gas (e.g., neutral molecules). In certain instances, a modifier and/or dopant may be introduced into the gas flow that drives the equilibrium toward a desired homogeneous cluster ion population. Homogeneous clusters have well-defined DMS characteristics.

Once the sample ions enter the DMS inlet 220, the voltage source applies RE (Vrf) and DC (Vc) voltages to at least one of a pair of filter electrodes 216 and 218 (Step 304). With the applied RF and DC voltages, the filter electrodes 216 and 218 generate an electric field in the flow path between the pair of filter electrodes 216 and 218 (Step 306). In certain embodiments, the controller 228 controls the RE and DC voltages applied from the voltage source 226 to the filter electrodes 216 and 218 so as to pass through the electric field a selected portion of the sample ions based on the mobility characteristics of the sample ions (Step 308). Some or all of the selected portion of sample ions that exit the DMS outlet 222 may then be received at a mass spectrometer 224 (Step 310) via the orifice 214. The transfer of ions from the DMS to mass spectrometer 224 may be effected by sealing the outlet of the DMS with the aperture 214 to establish a vacuum drag of gas from the DMS 204 into the mass spectrometer 224. The mass spectrometer 224 may employ any number of known techniques and operations using the ion optics assembly 230 and mass analyzer 232 to analyze and detect the sample ions from the DMS 204.

Figure 4:
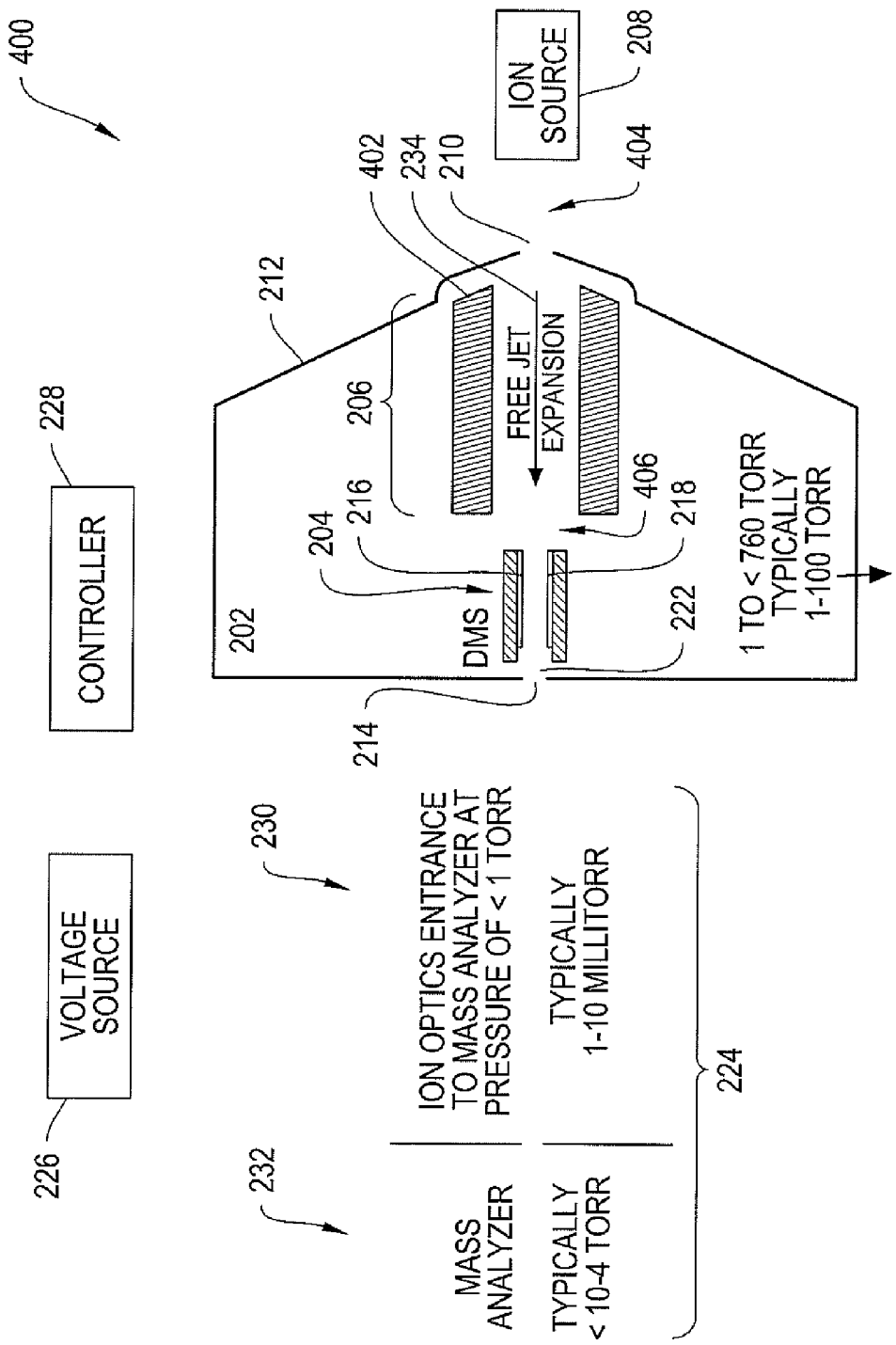
FIG. 4 shows a diagram of a mass analysis system as in FIG. 2 with an ion guide according to an illustrative embodiment of the invention.

FIG. 4 shows a diagram of a mass analysis system 400 like system 200 in FIG. 2 with the addition of an ion guide 402 according to an illustrative embodiment of the invention. In certain embodiments, the ion guide 402 is included in the low pressure collision region 206 to focus and direct sample ions from the vacuum inlet 210. In the region between aperture 210 and ion guide 402, a potential may be applied to accelerate the sample ions and facilitate declustering and/or desolvation of the sample ions before entry into the DMS 204. The ion guide may include a QJET®. Under certain conditions, a potential difference between the vacuum inlet and the QJET® may enable acceleration and declustering of sample ions from the ion source 208. The system may also include a free jet expansion due to the pressure differential across the vacuum inlet/orifice 210 that also propels ions through the ion guide 402 toward the DMS inlet 220. In one embodiment, the ion guide 402 may include a quadrupole ion guide. In another embodiment, the ion guide 402 may include dual ion guides or a plurality of ion guides to effect acceleration of sample ions and declustering. The inclusion of an ion guide 402 enables the introduction of substantially dry sample ions into the DMS inlet 220. The ion guide 402, operating as an ion focusing element, may focus and guide sample ions entering the vacuum chamber 202 via the vacuum inlet 210 toward the DMS inlet 220. Collisions between the sample ions and a collision gas may occur before, within, or after the ion guide 402. The ion guide 402 may include RF rods, DC lenses, and/or RF lenses.

In one embodiment, the vacuum chamber 202 includes an intermediate region 406, located downstream of the ion guide 402 and upstream of the DMS 204. The intermediate region may include some type of ion control element such as, without limitation, a second ion guide and/or an RF multipole, or the like to further effect control of the sample ions in the vacuum chamber 202. In addition, a lens element may be included in region 406 to limit electrical interference for the RF potentials applied to the ion guide 402 and DMS 204.

Thus, in certain embodiments, the DMS 204 is moved from a location within the atmospheric pressure source region 404 to a new location within the vacuum region and/or chamber 202 of the system 400. This may be accomplished on systems that include a QJET® or dual QJET® ion optics configuration. For instance, on the AB Sciex 5500 QTRAP platform, the DMS 204 could be located in the first vacuum region downstream of a slightly shortened QJET quadrupole ion guide. With this configuration, the DMS/MS system, such as the system 400, would retain the identical desolvation/declustering configuration of a standard 5500 QTRAP® platform, however, ion filtering can be accomplished for dry ions downstream of the QJET®. Other benefits and advantages of employing a low pressure collision region 206 and/or ion guide 402 upstream of the low pressure DMS 204 may include:

- Complete elimination of sensitivity losses due to solvent clustering within the source region and ion source 208.
- Dramatically simplified DMS power supply that requires much lower AC amplitudes since the same E/N ratio would be achieved in a region of much lower number density.
- Elimination of any ion optics crosstalk within the QJET® region, since ion filtering would occur downstream from this optic.
- Simplification of the design of a tandem DMS as "doped separations" can be performed in the atmospheric pressure curtain chamber with a standard DMS.
- Separations under the presence of modifiers (dopants) are done according to a cluster/decluster model and/or process to be discussed later herein. A collision region that strips the clusters and then allows for a second mobility based separation based on a second different separation mechanism, e.g., hard sphere collision model, to be discussed later herein. The use of two orthogonal separation mechanism enhances the specificity of the analysis process.

In certain embodiments, at least a portion of the vacuum chamber 202 and/or DMS 204 can be operated at about 50 to about 760 Torr. In certain configurations, the DMS can operate from about 200 to about 500 Torr. In certain configurations, the DMS can operate at about 200 Torr. In certain embodiments, the DMS can be operated at about 2-4 Torr. The DMS 204 may be operated at less than or equal to about 100 Torr, 50 Torr, 25 Torr, 10 Torr, 5 Torr, 4 Torr, 2 Torr, 1 Torr, 0.5 Torr, 0.3 Torr, and/or 0.1 Torr. However, at a certain pressure setting, due to some signal loss, the Vrf waveform frequency and/or gap height between DMS filter electrodes 216 and 218 may need to be adjusted to account for the increased oscillation amplitude of the sample ions in the DMS 204 that may occur due to reduced pressure.

Alternatively, in certain embodiments, an additional vacuum stage can be included prior to region 202. The pressure can be set to about 50 to 760 Torr, and the region can include the DMS and a declustering region as well as an optional ion guide. With this configuration, the region 202 would not include a DMS.

Figure 5A:
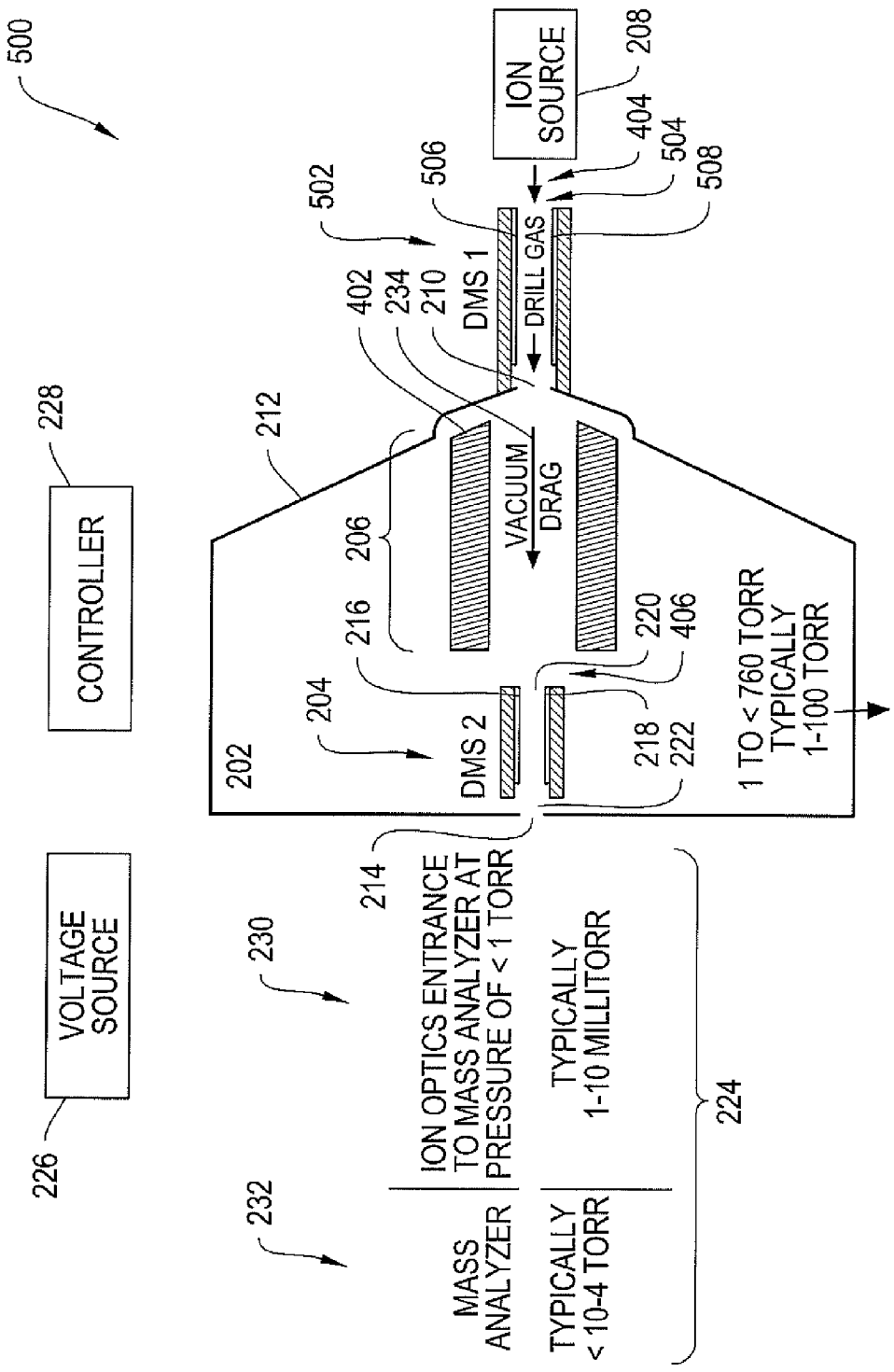
FIG. 5A shows a diagram of a mass analysis system as in FIG. 4 with an atmospheric pressure DMS pre-filter according to an illustrative embodiment of the invention.

FIG. 5A shows a diagram of a mass analysis system 500, like the system 400 shown in FIG. 4, with an additional atmospheric pressure DMS 502 pre-filter according to an illustrative embodiment of the invention. The DMS 502 is located in the atmospheric pressure source region 404 and receives sample ions from the ionization source 208 at the DMS inlet 504. In the same manner as DMS 204, the DMS 502 passes through selected sample ions by applying an asymmetric RF field and DC compensation field between the DMS filter electrodes 506 and 508. The voltage source, under the control of controller 228, applies both a Vrf and Vc voltage to at least one of the DMS filter electrodes 506 and 508 to generate the RF and DC electric field. Sample ions passing through the filtering electric field of the DMS 502 are separated based upon their ion mobility characteristics in the drift gas and the electric field of the DMS 502. FIG. 5A also shows that the ion flow 234 in the low pressure collision region 206 is at least partially due to a vacuum drag created by the difference in pressure from the DMS 502, operating at or near atmospheric pressure, and the vacuum chamber 202, operating at about 1 Torr to about atmospheric pressure.

The mass analysis system 500 advantageously combines an atmospheric pressure DMS 502 with a low pressure DMS 204 to combine the benefits of performing ion mobility based separation at both conditions. This can provide a dramatic improvement in separation power and peak capacity when the separation conditions are different in the 2 mobility analyzers.

Ion separation in DMS occurs as a result of differences in ion mobility at high and low electric fields. The field dependence of the ion mobility can be symbolically represented as the α function, as shown in the following equation, $$\alpha\left(\frac{E}{N}\right) = \frac{K(E) - K(0)}{K(0)}$$

where K(E) is the high field mobility and K(0) is the low field mobility. Thus the alpha function describes changes that occur to the mobility coefficient with electric field strength at constant gas number density. FIG. 12 illustrates the 3 general types of mobility behavior observed in a DMS, including monotonically increasing α (Type A), monotonically decreasing α (Type C), and first increasing then decreasing α (Type B).

The addition of polar modifiers to the transport gas within a DMS cell can improve selectivity as a result of cluster formation. Different chemical species cluster to different extents with chemical modifiers, and this imparts additional selectivity. The asymmetric waveform used in DMS varies between high field and low field regimes at a rate in the MHz range. This variation can be modeled as a field-dependent effective temperature synchronous with the Vrf field because of the high collision frequency at atmospheric pressure. When ion-neutral clustering is occurring to a significant extent, the time-varying effective temperature can cause a time-varying change in ion size and, therefore, a synchronous change in ion-mobility cross-section. Ions are clustered during the low field portion of the waveform and undergoing declustering due to heating during the high field portion of the waveform. The extent of clustering and the relative change in mobility due to clustering dictates the magnitude of Vc shift observed for the compounds, and the structural and chemical differences of compounds leads to a spread in peak position in the presence of clustering modifiers or dopants. This reversible cluster formation provides a method for the amplification of differential mobility effects in DMS. Because the change in cluster number occurs between the low and high field regimes during the SV waveform in DMS, the differential mobility is greatly enhanced.

In the absence of clustering modifiers, the hard sphere collision model can be used to predict the motion of colliding particles at high separation fields. Such predictions are widely used in molecular dynamics (MD) to understand and predict properties of physical systems at the particle level. The hard sphere collision model is based on the kinetic theory of gases in which, unlike the viscous damping models, the individual collisions between ion and gas particles are modeled. The expected frequency of collisions, measured as a distance (the mean-free-path) is predicted by the kinetic theory of gases as a function of the known pressure, temperature, and collisional cross sections of colliding particles. Collisions between ion and gas particles result in positive and negative energy transfers as well as scattering (deflection of ion velocity vectors), or even absorptions (e.g. in electron-gas collisions). The energy transfers provide for the kinetic cooling of a fast moving ion as well as the kinetic heating of a slow moving ion. Usually, colliding particles are treated as hard spheres. Generally, the background gas is non-stationary and has a Maxwell-Boltzmann distribution of velocities, which can be a function of temperature.

Such a configuration of an atmospheric pressure DMS 502 with a low pressure DMS 204, in combination with the mass spectrometer 224, provides for enhanced system 500 analysis selectivity. Such solution as in system 500 can simplify the incorporation of DMS into existing analyzer instruments such as, for example, the QTRAP® 5500 system, and provide substantial improvements in detection limits. This will increase the number of assays where DMS and ion mobility based filtering is useful.

In some embodiments, the region 202 may not include an RF ion guide. For these embodiments, only a DMS would be included. The DMS can include a plurality of filter electrode pairs. As shown in mass analysis system 550 of FIG. 5B, the DMS can comprise four electrodes, and the separation voltage can be applied across two of the electrodes. A focusing potential can be applied to the other two electrodes.

FIG. 6 shows a diagram of a mass analysis system 600, like the system 500 shown in FIG. 5A, with a clustering and/or reaction region 612 prior to the atmospheric pressure DMS 502 according to an illustrative embodiment of the invention. The mass analysis system 600 also includes a curtain plate 602, a curtain chamber 604, curtain gas inlet 606, curtain gas control valve 608, curtain gas source 610, and aperture 614.

The curtain plate 602 may be configured to direct the curtain gas flow 616 and 618 out of the aperture 614 and towards the ion source 208. In one embodiment, a high-purity curtain gas (e.g., $N_2$) flows between curtain plate 602 and vacuum plate 212 and out of the orifice 614 to provide a counter flow of gas that aids in keeping the mass analysis system 600 clean by desolvating and evacuating large neutral particles. The counter current gas flow (e.g., curtain gas) serves to decluster ions and prevent neutrals from entering the curtain chamber 604 and reaction region 612.

In operation, a curtain gas is delivered to the curtain chamber 604 from a source 610 via a control valve 608 and inlet 606. In addition to the curtain gas, the source 610 may provide a clustering reagent (e.g., a dopant or modifier) with the curtain gas. The reagent may be in the form of a gas, vapor, and/or liquid. By including a clustering reagent, the system 600 enables selected clustering of the sample ions in the reaction/clustering region 612 prior to ion mobility based filtering by the DMS 502.

Thus, the DMS 502 performs ion mobility based filtering and/or separation consistent with the clusterization model. Under the clusterization model (shown as the Type A curve in FIG. 12), the alpha function becomes increasingly positive, indicating that the mobility under high field conditions is getting larger as an ion becomes smaller with increasing amounts of declustering. The mobility during the low field portion of the waveform becomes smaller relative to the high field condition because the ion is larger and highly clustered. The declustering mechanism dominates the separation process and the selectivity achieved is highly influenced by the chemical characteristics of the ion in relation to its immediate surroundings. Higher fields typically improve the declustering which accentuates the difference in the state of the ion, and thus mobility, under the two field conditions. Clusterization model separations are considered to be chemically dominated separations (Type A).

The mass analysis system 600 enables tandem DMS operations, using atmospheric pressure DMS 502 and low pressure DMS 204 where the DMS 502 advantageously filters doped sample ions (e.g., reagent clustered sample ions) that were formed in the reaction/clustering region 612 due to mixing with the clustering reagent. But, after filtering by the DMS 502, the sample ions are then declustered in the low pressure collision region 206 to remove the clustering reagent and/or other clustering. Once declustering/desolvation is performed, the dry and/or declustered sample ions then are subjected to further ion mobility based filtering by the low pressure DMS 204.

Thus, the DMS 204 performs ion mobility based filtering and/or separation consistent with the hard sphere collision model. Under transport gas conditions where clustering and adduct ion formation are minimized or nonexistent, the behavior of the sample ions shift towards a Type C classification. Under high field conditions the mobility is decreasing relative to the low field condition which remains constant. In high fields and in the absence of clusters, the hard sphere collision (or rigid sphere scattering) mechanism becomes dominant. At high interaction energies, the short-range repulsive potential becomes important, resulting in a decreasing mobility. In contrast to the situation with modifiers present, the separation process and the selectivity achieved is less under these conditions, since it has more to do with collision dynamics. The negative shift in a shifts the compensation voltage in the opposite direction of what is observed when clustering phenomena dominate. The sample ions that pass through the second DMS 204 are then analyzed and detected by the mass spectrometer 224.

Figure 5B:
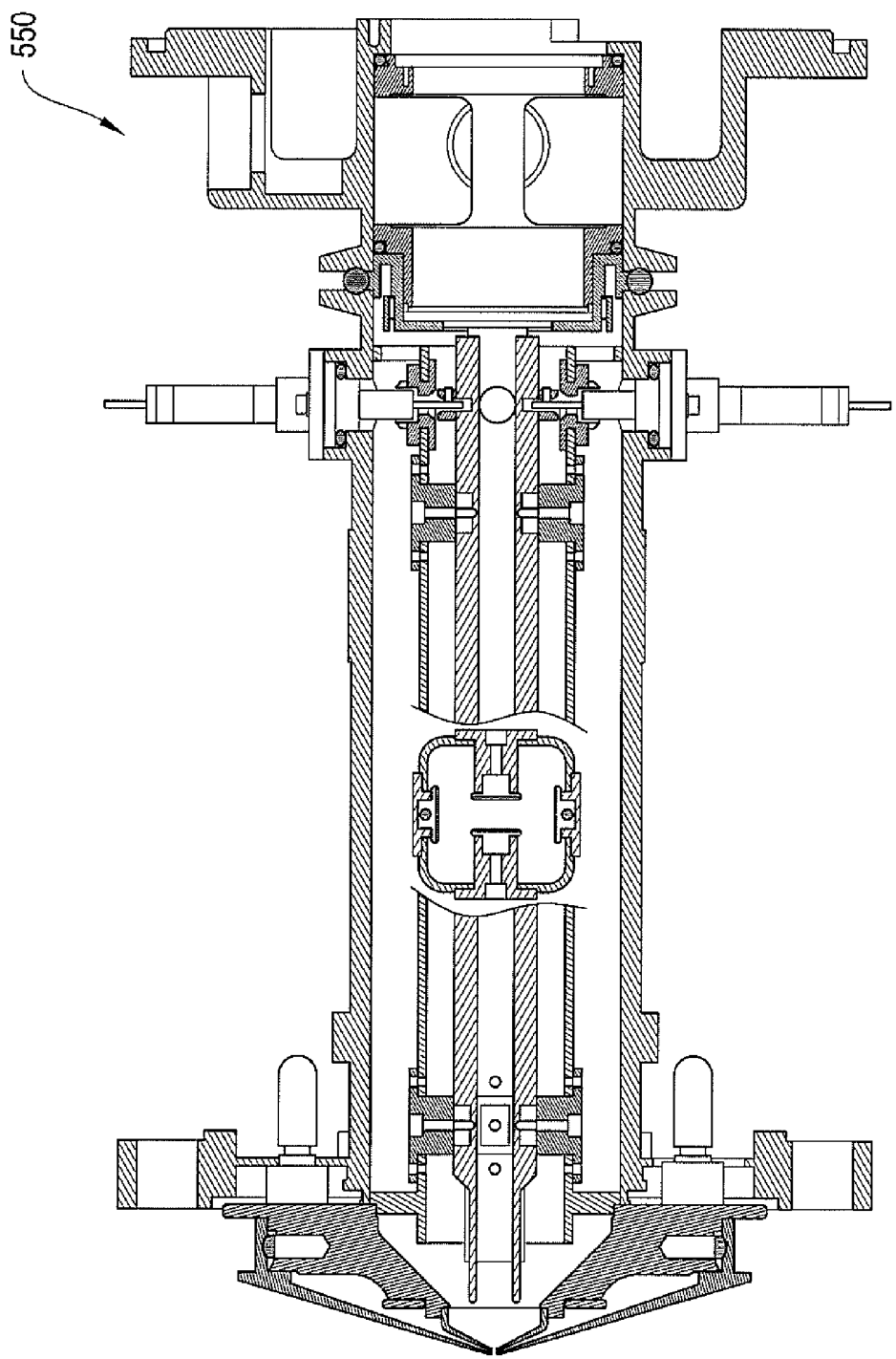
FIG. 5B shows a diagram of a mass analysis system as in FIG. 5A but without an RF ion guide, and a DMS comprising four electrodes according to an illustrative embodiment of the invention.

Thus, the configuration of the system 600 illustrates an enhanced design concept for a tandem DMS system. Accordingly, a DMS analyzer, e.g., DMS 204, may be located within the first reduced vacuum pressure stage, e.g., vacuum chamber 202, with an additional DMS analyzer, e.g., DMS 502, located within an atmospheric pressure region between the curtain plate 602 and gas restricting orifice 210. In this fashion, modifiers may be added in the typical manner to the curtain gas stream to provide a DMS separation based upon clustering modifiers. As demonstrated, the clusters are lost upon expansion into the first vacuum chamber 202, and this can be further facilitated by increasing the potential difference between the orifice 210 and QJET® ion guide 402. Subsequently, a second ion mobility based separation can be achieved within the first vacuum chamber 202, in the absence of modifiers. The tandem mobility analyzer, e.g., system 600, can provide a substantial improvement in mobility peak capacity over a single DMS configuration. Hence, the transmitted ion population is modified between the stages of DMS mobility based separation. In addition, if desired, ions may be fragmented by application of a high potential difference between the orifice 210 and QJET ion guide 402 to provide additional selectivity. This workflow would involve mobility selection of a particular ion in DMS 502, followed by fragmentation in the interface, e.g., low pressure collision region 206, followed by mobility selection in DMS 204 of a particular daughter ion. It will be apparent to those skilled in the art that the RF ion guide 402 can be removed, and the DMS can comprise for electrodes as shown in FIG. 5B.

FIGS. 7A-C includes plots 702, 704, and 706 of normalized ion intensity peaks in a DMS without reagent modifiers at various Vrf settings. As shown in the plots 702, 704, 706, is can be difficult to differentiate or separate the ion intensity peaks associated with this particular series of isobaric compounds under conditions where no dopant or modifier is added to sample ions passing through a DMS such as DMS 502. As shown in FIGS. 7A-C, there is a shift toward positive Vc values in all the compounds tested under these "dry ion" conditions.

FIGS. 15A-E includes plots 708, 710, 712, 714, and 716 of normalized ion intensity peaks in a DMS with reagent modifiers introduced at various Vrf settings. The various plots 708, 710, 712, 714, 716 illustrate the advantageous effect of adding a modifier, e.g., n-Propanol, 2-Propanol, and/or water, to the curtain gas which illustrate substantially improved peak capacity and substantially improved peak separation for many compounds in a DMS such as DMS 502. As shown in FIGS. 15A-E, there is a shift toward negative Vc values in all the compounds tested with a modifier and/or dopant added to the transport gas which is described based upon the clusterization model.

FIG. 8 shows a diagram of dopant introduction system 800 via a mixing chamber 802 according to an illustrative embodiment of the invention. The system 800 may be included in the source 610 of FIG. 6 or may be included in the system 600 in addition to the source 610. The system 800 also includes a curtain/transport gas inlet 804, a clustering reagent reservoir 806, and a curtain chamber inlet 808.

In operation, clustering reagent is stored in a liquid reservoir 806 and mixed in mixing chamber 802 with the curtain/transport gas. The mixture of curtain gas and modifier are then delivered via the inlet 808 to the curtain gas chamber 604 and, more particularly, to the reaction/clustering region 612. Conversely, the clustering reagent may be added to carrier/transport gas prior to introduction into the mixing chamber 802.

FIG. 9 shows a diagram of an alternative dopant introduction system 900 according to an illustrative embodiment of the invention. The system 900 includes a mixing region 902 within the curtain chamber 604, a curtain/transport gas inlet 904, and a clustering reagent reservoir 906. Instead of premixing the curtain and reagent in a mixing chamber 802 according to FIG. 8, in this embodiment, the clustering reagent and curtain gas are mixed in a mixing region 902 of the curtain gas chamber 604. Conversely, the clustering reagent may be added to carrier/transport gas prior to introduction into the mixing chamber 902.

FIG. 10 shows a diagram of a mass analysis system 1000, like the system 600 in FIG. 6, with a turbulent heated region 1002 according to an illustrative embodiment of the invention. The system 1000 also includes a clustering reagent inlet 1004, curtain gas inlet 1006, and reagent/curtain gas mixing region 1008. In some embodiments, the system 1000 employs a dopant introduction system like system 900 of FIG. 9. In other embodiments, the system 1000 employs a dopant introduction system like system 800 of FIG. 8. Alternatively, the clustering reagent may be added directly to carrier/transport gas prior to introduction into the system. The system 1000 also advantageously employs a turbulent heated region 1002 to enable turbulent heating of the sample ions from the ion source 208.

By heating the sample ions, declustering and/or desolvation of the sample ions is enhanced before introducing the sample ions into the DMS 502. One or more heating elements 1010 may be included in the heated region 1002 to generate a selected temperature for heating the sample ions. A heating element 1010 may include a resistive element. The controller 228 may control the application of current and/or voltage to a heating element 1010 via the voltage source 226 to regulate the temperature in the heated region 1002. One or more temperature sensors may be in communication with the controller 228 to enable the controller to regulate the temperature of the heated region.

The number and location of heating elements may vary in the system 1000. For example, one or more heating elements may be located in the atmospheric pressure ion source region 404, in the curtain chamber 604, in the vacuum chamber 202, in the intermediate region 406, in the low pressure collision region 206, or in any combination of the regions/locations within the system 1000. By employing one or more heated regions, such as turbulent heated region 1002, the sensitivity of the system 1000 is enhanced by improving declustering/desolvation at desired locations within the system 1000. The RF multipole 402 can be removed, and the DMS can comprise four electrodes as shown in FIG. 5B.

FIG. 11 is a graph 1100 including plots 1102 and 1104 of normalized ion intensity vs. compensation voltage when the inlet to the atmospheric pressure DMS is not heated and heated respectively (1102 includes the data without heat). Plot 1102 shows the Vc (CV) at about −2.5 volts with substantial peak tailing which is likely due to undesired clustering from moisture, for example, due to wet spray from an electrospray ionization source. Plot 1104 shows a shift in Vc to about 0 volts with an increased ion intensity and improved peak shape after the DMS inlet is heated, which illustrates how heating can improve declustering and/or desolvation and enhance analysis system sensitivity such as for system 1000. As described earlier, heterogeneous clusters can be eliminated or reduced by employing heating techniques.

RF ion heating and bulk gas heating effects in DMS are closely related. For example, bulk heating can reduce the heterogeneous cluster ion population in an ion analyzer system. The goal is to desolvate/decluster electrospray generated clusters, and then recluster with a desired gas-phase reaction forming a homogeneous population in the DMS cell and/or filter. Heat transfer is highly efficient at atmospheric pressure due to the high frequency of molecular collisions and radiative heat transfer. Various means for heating the cluster ions in the gas prior to the entrance of a DMS filter can be envisioned in addition to RF heating just described. One approach, uses a wall-less mixing region with counter-current gas flows to accomplish this. Hot desolvation gas containing a mixture of the inert nitrogen curtain/transport gas with the modifier/dopant flows counter to the incoming ion clusters and source gas in a wall-less area.

Flow can be non-laminar in this region which maximizes the residence time of the cluster ion species in the heated region to drive desolvation to the extent possible. The background gas may have a high concentration of modifier/dopant that drives the equilibrium toward the desired homogeneous cluster ion population. The outflow of drying gas in front of the DMS analyzer region also helps to prevent neutral solvents and very large droplets from entering and contaminating the mobility analyzer region. Heterogeneous ion clusters can be reduced using this approach. In certain embodiments, the controller 228 controls various parameters of the analysis process such as, without limitation, dopant concentration, temperature, flow rate, Vc, Vrf, and pressure within the various portions of the analyzer system, such as system 1000.

FIG. 12 is a graph of the alpha behavior for type A, B, and C ion mobility behavior. The Type A curve is associated with the clusterization model and exhibits a monotonic increase in alpha ($\alpha$) with the increase in field strength. The Type C curve is associated with the hard sphere collision model and exhibits a monotonic decrease in alpha with the increase in field strength. The Type B curve is associated with a bi-model mode (combination of Type A first, then Type C) where an initial increase then decrease in alpha occurs with an increase in field strength. As is demonstrated in these curves, the classification describes the dominant separation mechanism at play which in turn is controlled by the degree to which an ion is clustered or adducted to neutral molecules. Types A and C represent limits (extremes) where one mechanism dominates, and type B is observed under conditions such that a mixture of mechanisms is apparent.

Type A

Under Type A conditions and/or clusterization model, the alpha function becomes increasingly positive indicating that the mobility under high field conditions is getting larger as the ion becomes smaller with increasing amounts of declustering. The mobility during the low field portion of the waveform becomes smaller relative to the high field condition because the ion is larger and highly clustered. The declustering mechanism dominates the separation process and the selectivity achieved is highly influenced by the chemical characteristics of the ion in relation to its immediate surroundings. The alpha function rapidly climbs with increasing Rf field.

Type C

Under transport gas conditions where clustering and adduct ion formation are minimized or nonexistent (e.g., low pressure condition), the behavior of a sample ion shifts to a Type C classification and/or hard sphere collision model. With increasing field strength, the alpha function becomes increasingly negative. Under high field conditions the mobility is decreasing relative to the low field condition which remains constant. In high fields and in the absence of clusters, the rigid sphere scattering mechanism becomes dominant. At high interaction energies, the short-range repulsive potential becomes important resulting in a decreasing mobility. In contrast to the situation with modifiers present, the separation process and the selectivity achieved is less under these conditions, since it has more to do with collision dynamics.

Type B

Under inert transport gas conditions, the separation mechanism exhibits declustering behavior at low Rf amplitudes. Compounds that exhibit this behavior are present as adducts or clusters even under dry transport gas conditions. As the field strength increases, the Vc reverses direction and shifts toward positive values exhibiting a negative trend in alpha. This bimodal behavior is illustrated in the Type B alpha plot of FIG. 12.

In a dry inert gas flow, the alpha function for a given ion within a DMS is constant, regardless of instrumental variations such as potential and pressure. This principal forms the basis for DMS sensors employing ionization sources such as nickel 63 beta emitters in combination with ion current detectors. The correlation of peaks at various Vc positions at different locations in the world necessitates this. The practical consequence of this is that DMS peak capacity can not be significantly improved by simply providing two DMS filters and conducting two separations on the same ion population rather than one. Dramatic improvements in peak capacity can require significant alterations of the alpha function for a given ion population between the two separations. Therefore, in one embodiment of the current invention, an ion population passes through a reaction/cluster region and is carried through a first DMS with a transport gas containing clustering modifiers. The $\alpha$ function for the clustered ions may have the form of the Type A behavior illustrated in FIG. 12. The selected subset of the ion population then passes through the dissociation region where the equilibrium is driven towards the declustered ion species. Finally, a second DMS separation is carried out on the subset of ions, where the $\alpha$ function may display either Type B or Type C behavior. FIG. 13 shows an example of the transformation of the $\alpha$ function for norfentanyl ions. The trace labeled i) shows the alpha function for this ion under modified DMS separations where 1.5% 2-propanol was added to the nitrogen transport gas. The trace labeled ii) shows a radically different alpha function that is obtained when operating with nitrogen transport gas. The compound dependencies observed in the alpha functions under the two different conditions present the opportunity to dramatically improve peak capacity.

FIGS. 14A-C show the alpha functions for a series of ion separations in a DMS. FIG. 14A shows chemically modified separations using 2-propanol modifier, while FIGS. 14B and 14C show separations with inert nitrogen transport gas, respectively. In the presence of the clustering modifier, 36 compounds showed predominantly Type A behavior with positive values for the alpha function. In the absence of the clustering modifier, none of the 36 ions displayed Type A behavior, with all of them displaying a shift towards negative alpha values at high field. Under the instrumental conditions used to gather these data points, the observed compensation voltages Vc for the chemical species were predominantly negative for the modified separation and positive for the inert gas separation. In a number of cases, peaks that were not separated in the absence of modifiers were separated in the DMS that had modifiers in the transport gas flow. In a few cases, peaks that were not separated with the chemically modified separation were separated in the DMS that used inert transport gas. This simple example illustrates the peak capacity improvements that are possible when the alpha functions for a population of ions are dramatically altered between DMS separations in a tandem device. While this example describes altering the alpha function by changing the concentration of clustering modifiers in the transport gas flow, it will be apparent to those of skill in the relevant arts that the alpha function may also be altered in other ways including but not limited to a) maintaining a constant concentration of clustering modifier and varying the temperature within the two DMS analyzers to effect the degree of clustering, altering the transport gas composition without adding liquid modifiers, and fragmenting the ion of interest in the dissociation region such that the ion monitored in the second DMS has a different m/z than the ion monitored in the first DMS cell.

It will be apparent to those of ordinary skill in the art that certain aspects involved in the operation of the controller 228 may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, or flash memory device having a computer readable program code stored thereon. It will also be apparent to those of skill in the relevant art that the dissociation region may comprise other means of heating ions including a source of radiation such as a laser, or other devices.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

What is claimed is:

1. A sample analysis system comprising:
 a first pressure region operating at a pressure of about atmospheric pressure or greater including:

a first DMS filter for receiving sample ions from an ion source and passing through a first set of selected sample ions;

a dopant inlet, in communication with the first pressure region, for introducing at least one reagent, said dopant inlet being fluidly connected to a reservoir of the at least one reagent, and a second pressure region, in communication with the first pressure region, operating at less than about atmospheric pressure including:

a dissociation region configured to accelerate the first set of selected sample ions and collide the first set of selected sample ions with a collision gas, and a second DMS filter for passing through a second set of selected sample ions.

2. The system of claim 1 comprising: a third pressure region, in communication with the second pressure region, operating at less than about 1 torr including: an ion optics element for receiving the second set of selected sample ions.

3. The system of claim 2 comprising: a fourth pressure region, in communication with the third pressure region, operating at less than about $10^{-4}$ torr including: a mass analyzer.

4. The system of claim 1 comprising a gas inlet, in communication with first pressure region, for introducing at least one of a curtain gas and a transport gas.

5. The system of claim 1 comprising at least one heated region configured to perform at least one of i) declustering ions, ii) desolvating ions, iii) accelerating the reclustering of ions with reagents, and iv) shifting the clustering equilibrium for ions with dopant or reagents.

6. The system of claim 5 comprising at least one adjustable heating element for controlling the temperature in the at least one heated region.

7. The system of claim 1 comprising a heated region located within the first or second pressure region, wherein the heated region is configured to perform at least one of remove unwanted clusters of the sample ions and accelerate reclustering of the sample ions with the at least one reagent.

8. The system of claim 1 comprising a reaction region in the first pressure region for clustering a portion of the sample ions using the at least one reagent.

* * * * *